(12) United States Patent
Jevons et al.

(10) Patent No.: US 6,804,679 B2
(45) Date of Patent: Oct. 12, 2004

(54) SYSTEM, METHOD, AND USER INTERFACES FOR MANAGING GENOMIC DATA

(75) Inventors: Luis Jevons, Sunnyvale, CA (US); Derek Bernhart, Lafayette Hill, PA (US); Conrad G. Sheppy, Redwood City, CA (US)

(73) Assignee: Affymetrix, Inc., Santa Clara, CA (US)

( * ) Notice: Subject to any disclaimer, the term of this patent is extended or adjusted under 35 U.S.C. 154(b) by 193 days.

(21) Appl. No.: 09/683,982

(22) Filed: Mar. 8, 2002

(65) Prior Publication Data

US 2002/0128993 A1 Sep. 12, 2002

Related U.S. Application Data

(60) Provisional application No. 60/274,988, filed on Mar. 12, 2001.

(51) Int. Cl.[7] ............................................. G06F 17/30
(52) U.S. Cl. ............................ 707/102; 707/10; 707/4; 707/1; 707/2; 707/3
(58) Field of Search ........................ 700/90; 250/458.1, 250/559.06; 356/318; 435/6; 705/14, 500; 707/4, 10, 1, 102, 3, 2; 600/407, 316

(56) References Cited

U.S. PATENT DOCUMENTS

| | | | | |
|---|---|---|---|---|
| 5,553,616 A | * | 9/1996 | Ham et al. .................. 600/316 |
| 5,953,727 A | | 9/1999 | Maslyn et al. |
| 5,978,804 A | * | 11/1999 | Dietzman .................... 707/10 |
| 6,188,783 B1 | | 2/2001 | Balaban et al. |
| 6,203,990 B1 | * | 3/2001 | Fahy .............................. 435/6 |
| 6,460,041 B2 | * | 10/2002 | Lloyd .......................... 707/10 |
| 6,643,015 B2 | * | 11/2003 | Weiner ....................... 356/318 |
| 6,650,411 B2 | * | 11/2003 | Odoy et al. ................. 356/318 |
| 2001/0037331 A1 | * | 11/2001 | Lloyd ............................. 707/4 |
| 2001/0054046 A1 | * | 12/2001 | Mikhailov et al. .......... 707/500 |
| 2002/0024026 A1 | * | 2/2002 | Kaushikkar ............ 250/559.06 |
| 2002/0074512 A1 | * | 6/2002 | Montagu et al. ......... 250/458.1 |
| 2002/0128908 A1 | * | 9/2002 | Levin et al. .................. 705/14 |
| 2002/0128993 A1 | * | 9/2002 | Jevons et al. .................. 707/1 |
| 2002/0129009 A1 | * | 9/2002 | Jevons et al. .................. 707/3 |
| 2002/0147512 A1 | * | 10/2002 | Bernhart et al. ............. 700/90 |
| 2002/0159057 A1 | * | 10/2002 | Odoy et al. ................. 356/318 |
| 2002/0159058 A1 | * | 10/2002 | Weiner ....................... 356/318 |
| 2003/0036087 A1 | * | 2/2003 | Kaushikkar et al. ........... 435/6 |
| 2003/0139659 A1 | * | 7/2003 | Dale et al. .................. 600/407 |
| 2003/0157545 A1 | * | 8/2003 | Jevons et al. .................. 435/6 |

FOREIGN PATENT DOCUMENTS

| WO | WO 9903048 A1 | * | 1/1999 | ........... G06F/17/30 |
|---|---|---|---|---|
| WO | WO 0201194 A1 | * | 3/2002 | ........... G01N/21/00 |
| WO | WO 0237209 A2 | * | 10/2002 | ........... G06F/17/30 |

* cited by examiner

*Primary Examiner*—Frantz Coby
(74) *Attorney, Agent, or Firm*—William R. McCarthy, III; Philip L. McGarrigle; Alan B. Sherr

(57) ABSTRACT

A data manager is described for providing a publish database for access by data mining tools and other data processing software applications. The data manager includes a results-for-publication identifier that identifies synthesized probe array results and spotted probe array results for publishing. This identification may be based, at least in part, on user selections. The data in the publish database is organized in accordance with an integrated database schema. The data manager may also include an experimental results registration processor that registers the synthesized probe array results and the spotted probe array results for publishing. This registration may be based, at least in part, on user selections. For example, a user may select certain probe array results from a graphical user interface displaying a tree of files containing probe array results from multiple experiments with synthesized and/or spotted probe arrays.

31 Claims, 14 Drawing Sheets

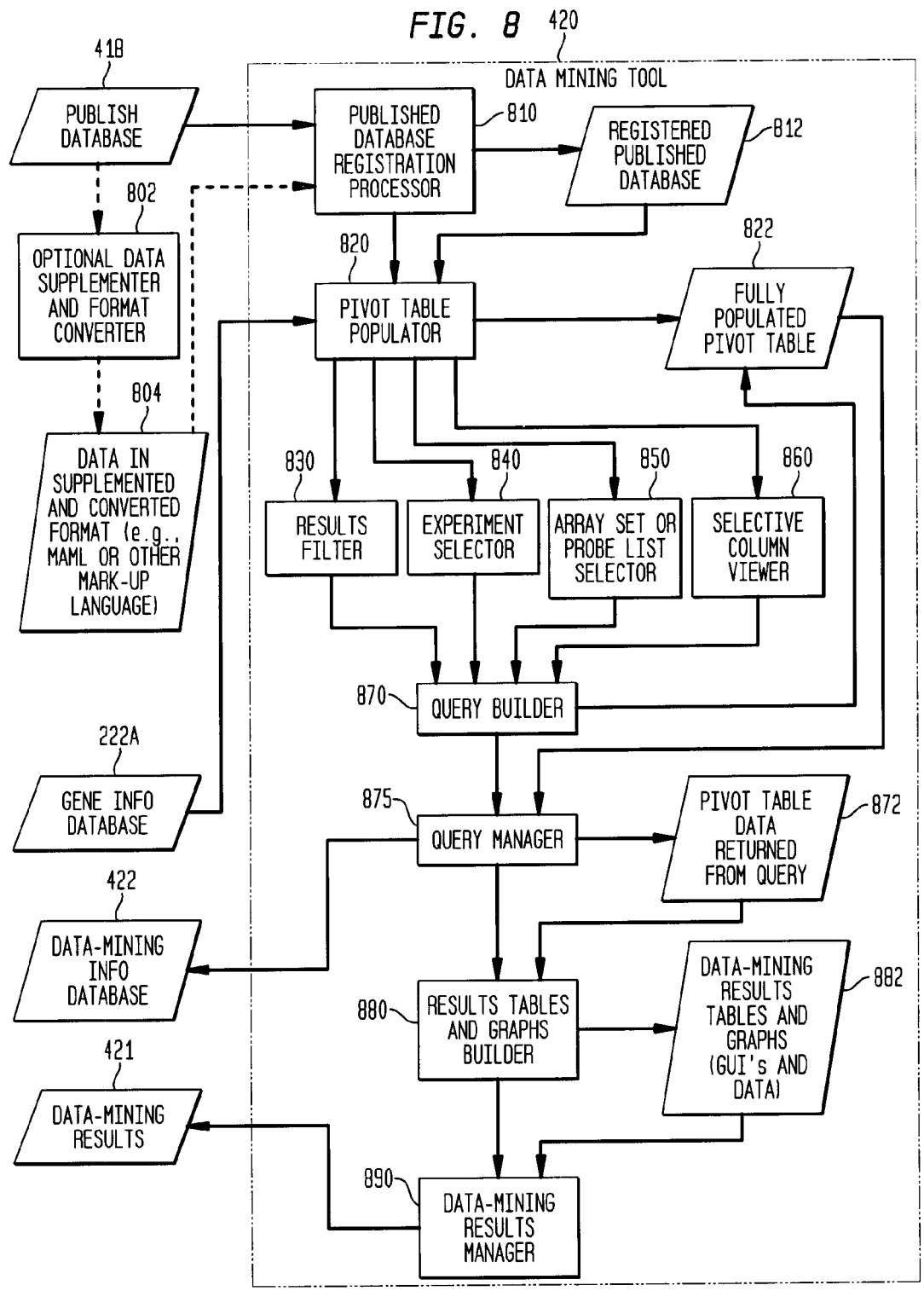

SYSTEM, METHOD, AND USER INTERFACES FOR MANAGING GENOMIC DATA

CROSS REFERENCE TO RELATED APPLICATIONS

This application claims priority from U.S. Provisional Patent Application No. 60/274,988, titled System, Method, and User Interfaces for Managing Genomic Data, filed on Mar. 12, 2001, which is hereby incorporated herein by reference in its entirety for all purposes.

COPYRIGHT STATEMENT

A portion of the disclosure of this patent document contains material that is subject to copyright protection. The copyright owner has no objection to the facsimile reproduction by anyone of the patent document or the patent disclosure exactly as it appears in the Patent and Trademark Office patent file or records, but otherwise reserves all copyright rights whatsoever.

BACKGROUND OF INVENTION

The present invention is related to systems, methods, and products for managing biological data generated by scanning arrays of biological materials.

Synthesized nucleic acid probe arrays, such as GeneChip® probe arrays available from Affymetrix, Inc. of Santa Clara, Calif., and spotted probe arrays such as those made using 417™ or 427™ Arrayers from Affymetrix, have been used to generate unprecedented amounts of information about biological systems. For example, the GeneChip® Human Genome U133 Set (HG-U133A and HG-U133B) from Affymetrix is available on two microarrays containing over 1,000,000 unique oligonucleotide features covering more than 39,000 transcript variants that represent more than 33,000 human genes. Analysis of expression data from such microarrays may lead to the development of new drugs and new diagnostic tools.

SUMMARY OF INVENTION

There is a demand among users of probe arrays for methods and systems for accessing, analyzing, and managing the vast amount of information collected using nucleic acid probe arrays or using other types of probe arrays. These methods and systems may include the use of software applications and related hardware that implement so-called data mining tools. The operations of these data mining tools typically are facilitated by organizing the data that they mine in appropriate formats. It often is desirable to employ data management applications to provide these formatting operations, as well as to provide other data management functions.

Systems, methods, and computer program products are described herein to address these and other needs. Reference will now be made in detail to illustrative, non-limiting, embodiments. Various other alternatives, modifications and equivalents are possible. For example, while certain systems, methods, and computer software products are described using exemplary embodiments for analyzing data from experiments that employ Affymetrix® GeneChip® probe arrays and/or spotted arrays made using arrayers from Affymetrix, these systems, methods, and products generally may be applied with respect to many other probe arrays and parallel biological assays.

In one embodiment, a data manager is described for providing a publish database. The word publish used as an adjective in this context refers to a database that is in a format, and/or organized in accordance with a schema, to facilitate access by data analysis applications, data mining applications, data reporting applications, other data processing applications, or any combination thereof. The word access in this context refers to storing, retrieving, or otherwise manipulating data. The word publish and its grammatical variants used as a verb in this context refer to formatting and/or organizing a database so that it is accessible as a publish database.

The data manager in these embodiments includes a results-for-publication identifier that identifies synthesized probe array results and spotted probe array results for publishing. This identification may be based, at least in part, on user selections. As used in this context, identifies and its grammatical variants is intended to be understood broadly. For example, a list of probe array results may simply be consecutively identified for publishing, or various criteria (based on time of experiment, type of experiment, a priority indicator representing the importance of the experiment, and so on) may be used to selectively identify probe array results for publishing or for publishing in a certain order. The data manager also includes a publisher that publishes the synthesized probe array results and the spotted probe array results in a publish database.

The data in the publish database may be organized in accordance with an integrated database schema. The term database schema refers to a scheme for relationships among database entities. In some implementations, the database scheme may include entity relationships among database objects. The database typically is a relational database. As is well known to those of ordinary skill in the relevant art, a number of tools exist for designing and documenting database schema, such as Erwin® software from Computer® Associates International, Inc. of Islandia, N.Y. The word integrated in this context means that both data in the publish database related to the synthesized probe array results and data in the publish database related to the spotted probe array results are included in the same database schema. One example of an integrated database schema is the AADM schema from Affymetrix, described below. In some implementations of these embodiments, the synthesized probe array results are in a first format, the spotted probe array results are in a second format, and the publish database is in a third format. That is, the publisher typically converts data from the first and second formats into a third format. The publisher typically stores the publish database in a memory unit of a computer. In these implementations, data in the publish database typically is addressable from a common reference address of the memory unit. Also, the publisher may store the publish database in the memory unit as one or more related files. These files may be related, for example, by using a common name and distinguishing the files based on different file extensions, or in accordance with any of a variety of other methods and techniques known to those of ordinary skill in the relevant art.

The data manager may, in some implementations, also include an experimental results registration processor that registers the synthesized probe array results and the spotted probe array results for publishing. This registration may be based, at least in part, on user selections. For example, a user may select certain probe array results from a graphical user interface displaying a tree of files containing probe array results from multiple experiments with synthesized and/or spotted probe arrays.

In accordance with other embodiments, a method is described for providing a publish database. The method includes the steps of identifying synthesized probe array results and spotted probe array results for publishing, and publishing the synthesized probe array results and the spotted probe array results in a publish database.

In yet other embodiments, a method is described for displaying a graphical user interface (GUI) in a computer display system having a processor coupled to a display device. Data is displayed on the display device in the GUI according to the following steps: (1) displaying a first frame in the GUI including a first set of graphical elements corresponding to at least one set of synthesized probe array results, and a second set of graphical elements corresponding to at least one set of spotted probe array results; (2) receiving a user selection of one or more of the first or second sets of graphical elements for publication in a publish database; and (3) displaying a second frame in the GUI including a third set of graphical elements corresponding to the publish database and, in relation thereto, a fourth set of one or more graphical elements corresponding to those of the first or second sets of graphical elements selected by the user. The first frame may include a data file view wherein the first and second sets of graphical elements are arranged in a first tree structure. The first set of graphical elements may be arranged in one branch of the first tree structure and the second set of graphical elements may be arranged in another branch of the first tree structure. In these implementations, at least one of the first set of graphical elements may correspond to a synthesized probe array result file; and at least one of the second set of graphical elements may correspond to a spotted probe array result file. Also, the second frame may include an active database view wherein the third set of graphical elements is associated with a root of a tree structure, and the one or more graphical elements corresponding to those of the first or second sets of graphical elements selected by the user are associated with branches attached to the root.

In these or other embodiments, the method of displaying the GUI may also include receiving a user activation of a publishing operation to be applied to one or more of the set of synthesized probe array results and/or one or more of the set of spotted probe array results. The step of receiving a user activation may include receiving a user selection of one or more of the fourth set of graphical elements, and causing the probe array results corresponding to the user-selected ones of the fourth set of graphical elements to be published to the publish database.

In another embodiment, a graphical user interface (GUI) is described for use with a computer display system having a processor coupled to a display device such that data is displayed on the display device in the GUI. The GUI includes: (1) a first frame including a first set of graphical elements corresponding to at least one set of synthesized probe array results, and a second set of graphical elements corresponding to at least one set of spotted probe array results; and (2) a second frame including a third set of graphical elements corresponding to the publish database and, in relation thereto, a fourth set of one or more graphical elements corresponding to those of the first or second sets of graphical elements selected by a user.

In a further embodiment, a computer program product is described for providing a publish database that, when executed on a computer system, performs a method comprising the steps of: (1) identifying at least one set of synthesized probe array results and at least one set of spotted probe array results for publishing; and (2) publishing the at least one set of synthesized probe array results and the at least one set of spotted probe array results as a first set of data in a publish database.

In yet a further embodiment, a computer system having a processor and a memory unit is described. A set of data management instructions, when stored in the memory unit and executed by the processor, performs a method for providing a publish database comprising the acts of identifying at least one set of synthesized probe array results and at least one set of spotted probe array results for publishing, and publishing the at least one set of synthesized probe array results and the at least one set of spotted probe array results as a first set of data in a publish database.

The above embodiments and implementations are not necessarily inclusive or exclusive of each other and may be combined in any manner that is non-conflicting and otherwise possible, whether they be presented in association with a same, or a different, aspect or implementation. The description of one implementation is not intended to be limiting with respect to other implementations. Also, any one or more function, step, operation, or technique described elsewhere in this specification may, in alternative implementations, be combined with any one or more function, step, operation, or technique described in the summary. Thus, the above implementations are illustrative rather than limiting.

BRIEF DESCRIPTION OF DRAWINGS

The above and further features will be more clearly appreciated from the following detailed description when taken in conjunction with the accompanying drawings. In the drawings, like reference numerals indicate like structures or method steps and the leftmost one or two digits of a reference numeral indicates the number of the figure in which the referenced element first appears (for example, the element 120 appears first in FIG. 1 and element 1010 first appears in FIG. 10). In functional block diagrams, rectangles generally indicate functional elements, parallelograms generally indicate data, and rectangles with a pair of double borders generally indicate predefined functional elements. In method flow charts, rectangles generally indicate method steps and diamond shapes generally indicate decision elements. All of these conventions, however, are intended to be typical or illustrative, rather than limiting.

FIG. 8 is a functional block diagram of one implementation of a data-mining-tool application such as may be included in the probe-array analysis applications executables and related data structures of FIG. 3;

DETAILED DESCRIPTION

Figure 4:
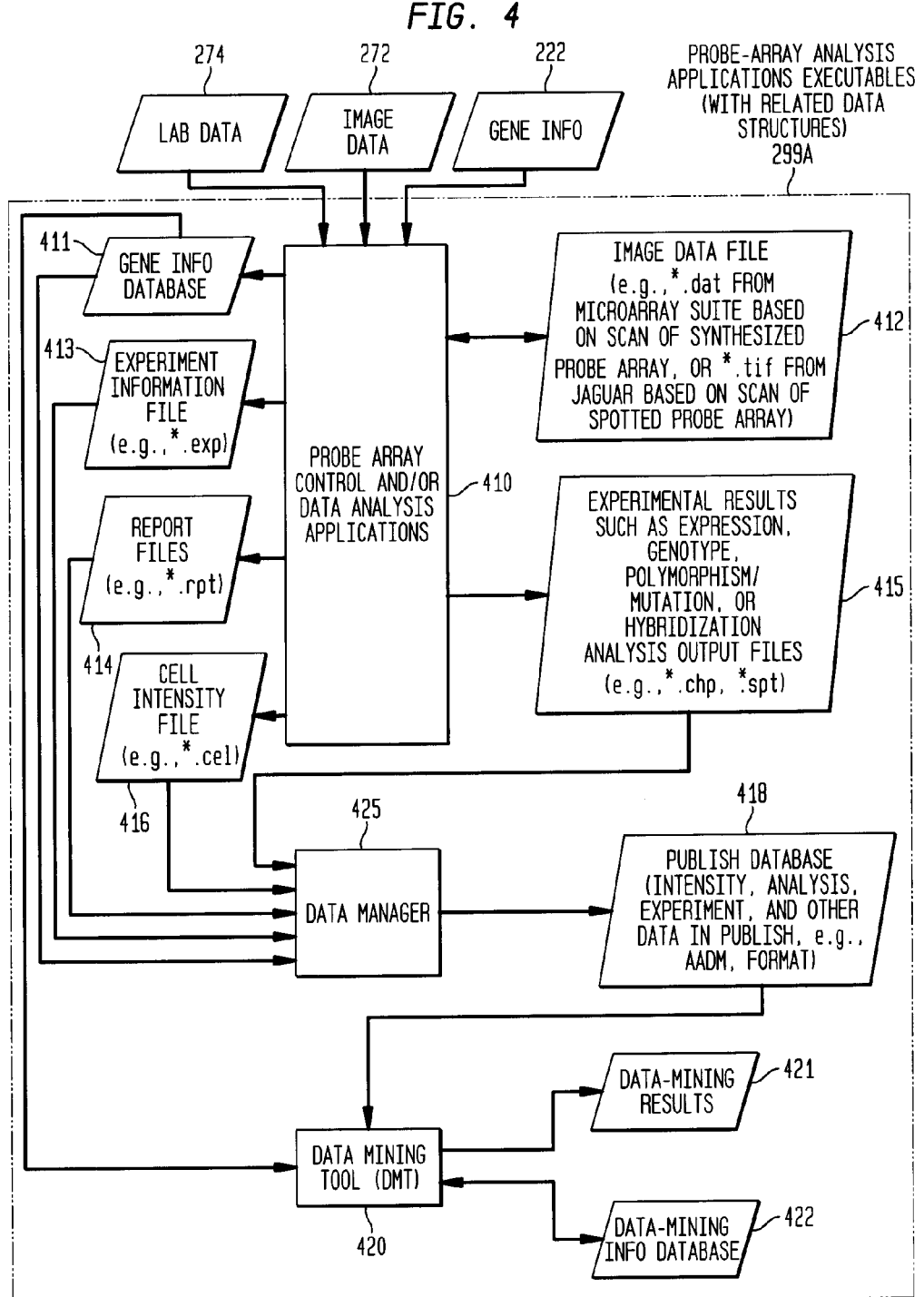
FIG. 4 is a functional block diagram of one embodiment of probe-array analysis applications executables and related data structures, including one embodiment of a software application in accordance with aspects of the present invention.

The present invention is described with respect to illustrative embodiments including methods, data processing and/or analysis systems, software program products, graphical user interfaces, or combinations thereof. One illustrative embodiment is referred to as data manager 425 as shown in FIG. 4 and as illustratively executed on user computer 100C of FIGS. 1 and 2. One illustrative, non-limiting, implementation of data manager 425 is Affymetrix® MicroDB™ available from Affymetrix, Inc. Data manager 425 of the illustrated implementation identifies synthesized probe array results and/or spotted probe array results for publishing. This identification typically is based on a user selection. Data manager 425 also publishes the synthesized and/or spotted probe array results in a publish database.

Figure 1:
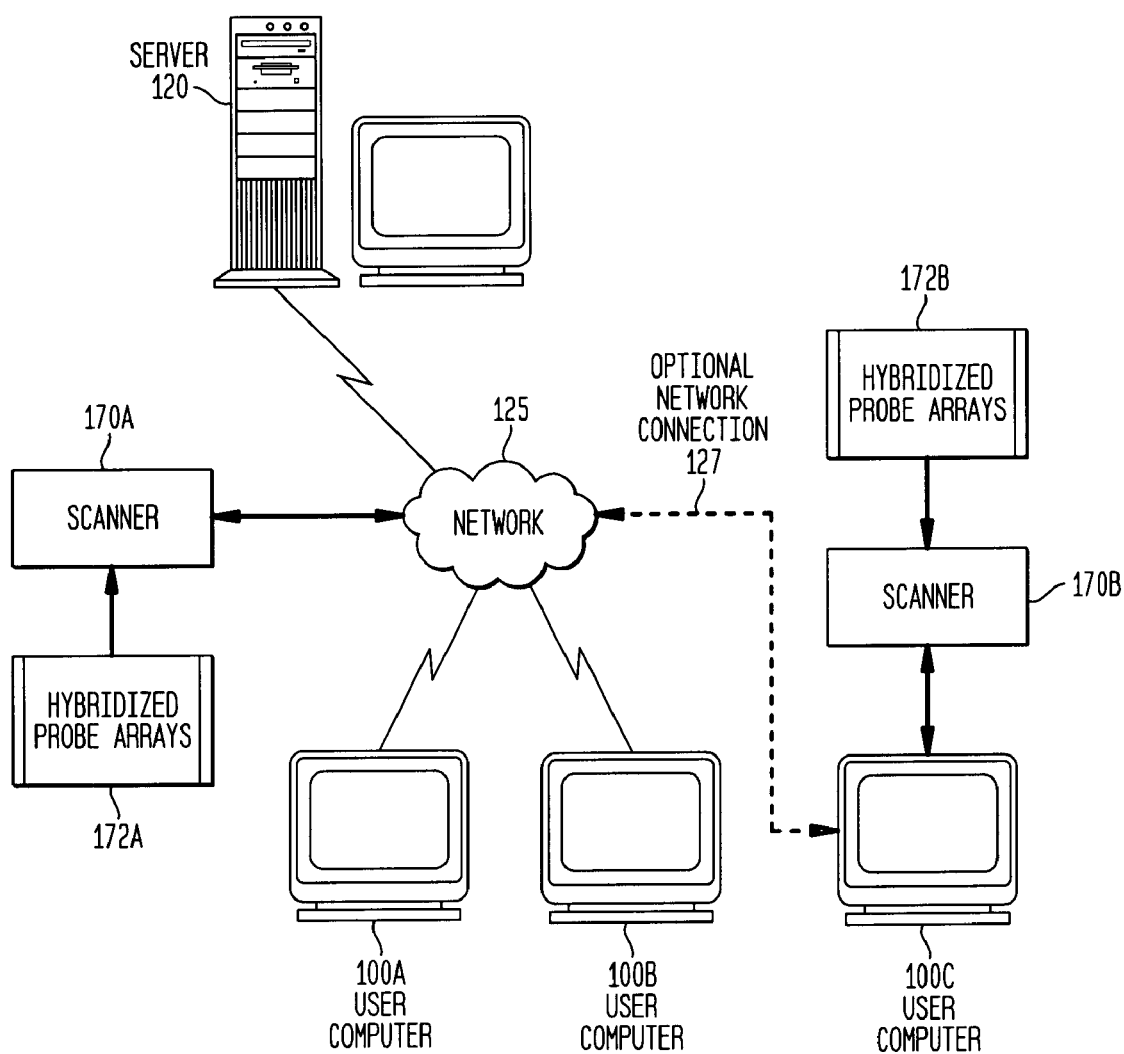
FIG. 1 is a simplified graphical representation of one embodiment of a computer network system over which data generated by a data manager application in accordance with aspects of the present invention may be transferred and/or processed.

Networked and/or Stand-Alone Operation: FIG. 1 is a simplified graphical representation of an illustrative computer network system over which data generated by data manager 425 may be transferred and/or processed. In particular, data generated by the scanning of hybridized probe arrays may be transferred and/or processed on or among server computer 120 (typically, a network-server class computer) and one or more of user computers 100A, B, and C (generally and collectively referred to as user computers 100). This data processing includes the scanning of synthesized and/or spotted probe arrays such as arrays 172A and 172B (generally and collectively referred to as arrays 172) by scanners such as scanners 170A and 170B (generally and collectively, scanners 170). Various combinations of stand-alone and networked data processing may be employed. For instance, user computer 100C may operate in a stand-alone mode by processing data scanned by scanner 170B from hybridized probe arrays 172B. Alternatively or in addition, as indicated by optional network connection 127, user computer 100C may access server 120, scanner 170A, or user computers 100A or 100B over network 125. This optional access may be used, for example, to store results of processing of scanned array data from probe arrays 172B, to compare those results to results obtained by other users from scanning probe arrays 172A, and for a variety of other reasons. Further details regarding server 120, network 125, and user computers 100 are provided below.

Hybridized Probe Arrays 172: Various techniques and technologies may be used for depositing or synthesizing dense arrays of biological materials on a substrate or support. For example, Affymetrix® GeneChip® arrays are synthesized in accordance with techniques sometimes referred to as VLSIPS™ (Very Large Scale Immobilized Polymer Synthesis) technologies. Some aspects of VLSIPS™ and other microarray manufacturing technologies are described in U.S. Pat. Nos. 5,424,186; 5,143,854; 5,445,934; 5,744,305; 5,831,070; 5,837,832; 6,022,963; 6,083,697; 6,291,183; 6,309,831; and 6,310,189, all of which are hereby incorporated by reference in their entireties for all purposes. The probes of these arrays typically consist of nucleic acids that typically are synthesized by methods that include the steps of activating regions of a substrate and then contacting the substrate with a selected monomer solution. As used herein, nucleic acids may include any polymer or oligomer of nucleosides or nucleotides (polynucleotides or oligonucleotides) that include pyrimidine and/or purine bases, preferably cytosine, thymine, and uracil, and adenine and guanine, respectively. Nucleic acids may include any deoxyribonucleotide, ribonucleotide, and/or peptide nucleic acid component, and/or any chemical variants thereof such as methylated, hydroxymethylated or glucosylated forms of these bases, and the like. The polymers or oligomers may be heterogeneous or homogeneous in composition, and may be isolated from naturally-occurring sources or may be artificially or synthetically produced. In addition, the nucleic acids may be DNA or RNA, or a mixture thereof, and may exist permanently or transitionally in single-stranded or double-stranded form, including homoduplex, heteroduplex, and hybrid states. Probes of other biological materials, such as peptides or polysaccharides as non-limiting examples, may also be formed. For more details, see U.S. Pat. No. 6,156,501, which is hereby incorporated by reference herein in its entirety for all purposes. A system and method for efficiently synthesizing probe arrays using masks is described in U.S. patent application Ser. No. 09/824,931, filed Apr. 3, 2001, that is hereby incorporated by reference herein in its entirety for all purposes. A system and method for a rapid and flexible microarray manufacturing and online ordering system is described in U.S. Provisional Patent Application, Serial No. 60/265,103, filed Jan. 29, 2001, that also is hereby incorporated herein by reference in its entirety for all purposes. Systems and methods for optical photolithography without masks are described in U.S. Pat. No. 6,271,957 and in U.S. patent application Ser. No. 09/683,374 filed Dec. 19, 2001, both of which are hereby incorporated by reference herein in their entireties for all purposes.

The probes of synthesized probe arrays typically are used in conjunction with biological target molecules of interest, such as cells, proteins, genes or EST's, other DNA sequences, or other biological elements. More specifically, the biological molecule of interest may be a ligand, receptor, peptide, nucleic acid (oligonucleotide or polynucleotide of RNA or DNA), or any other of the biological molecules listed in U.S. Pat. No. 5,445,934 (incorporated by reference above) at column 5, line 66 to column 7, line 51. For example, if transcripts of genes are the interest of an experiment, the target molecules would be the transcripts. Other examples include protein fragments, small molecules, etc. Target nucleic acid refers to a nucleic acid (often derived from a biological sample) of interest. Frequently, a target molecule is detected using one or more probes. A probe may be any of the molecules in the same classes as the target referred to above. As non-limiting examples, a probe may refer to a nucleic acid, such as an oligonucleotide, capable of binding to a target nucleic acid of complementary sequence through one or more types of chemical bonds, usually through complementary base pairing, usually through hydrogen bond formation.

Other techniques exist for depositing probes on a substrate or support. For example, spotted arrays are commercially fabricated, typically on microscope slides. These arrays consist of liquid spots containing biological material of potentially varying compositions and concentrations. For instance, a spot in the array may include a few strands of short oligonucleotides in a water solution, or it may include a high concentration of long strands of complex proteins. The Affymetrix® 417™ Arrayer and 427™ Arrayer are devices that deposit densely packed arrays of biological materials on microscope slides in accordance with these techniques. Aspects of these, and other, spot arrayers are described in U.S. Pat. Nos. 6,040,193 and 6,136,269; in U.S. patent application Ser. No. 09/683,298; and in PCT Application No. PCT/US99/00730 (International Publication Number WO 99/36760), all of which are hereby incorporated by reference in their entireties for all purposes. Other techniques for generating spotted arrays also exist. For example, U.S. Pat. No. 6,040,193 to Winkler, et al. is directed to processes for dispensing drops to generate spotted arrays. The "193 patent, and U.S. Pat. No. 5,885,837 to Winkler, also describe the use of micro-channels or micro-grooves on a substrate, or on a block placed on a substrate, to synthesize arrays of biological materials. These patents further describe separating reactive regions of a substrate from each other by inert regions and spotting on the reactive regions. The "193 and "837 patents are hereby incorporated by reference in their entireties. Another technique is based on ejecting jets of biological material to form a spotted array. Other implementations of the jetting technique may use devices such as syringes or piezo electric pumps to propel the biological material. Various other techniques exist for synthesizing, depositing, or positioning biological material onto or within a substrate.

Synthesized or spotted probe arrays typically are used in conjunction with tagged biological samples such as cells, proteins, genes or EST's, other DNA sequences, or other biological elements. These samples, referred to herein as targets, are processed so that they are spatially associated with certain probes in the probe array. For example, one or more chemically tagged biological samples, i.e., the targets, are distributed over the probe array. Some targets hybridize with at least partially complementary probes and remain at the probe locations, while non-hybridized targets are washed away. These hybridized targets, with their tags or labels, are thus spatially associated with the targets" complementary probes. The hybridized probe and target may sometimes be referred to as a probe-target pair. Detection of these pairs can serve a variety of purposes, such as to determine whether a target nucleic acid has a nucleotide sequence identical to or different from a specific reference sequence. See, for example, U.S. Pat. No. 5,837,832, referred to and incorporated above. Other uses include gene expression monitoring and evaluation (see, e.g., U.S. Pat. No. 5,800,992 to Fodor, et al.; U.S. Pat. No. 6,040,138 to Lockhart, et al.; and International App. No. PCT/US98/15151, published as WO99/05323, to Balaban, et al.), genotyping (U.S. Pat. No. 5,856,092 to Dale, et al.), or other detection of nucleic acids. The "992, "138, and "092 patents, and publication WO99/05323, are incorporated by reference herein in their entirety for all purposes.

To ensure proper interpretation of the term probe as used herein, it is noted that contradictory conventions exist in the relevant literature. The word probe is used in some contexts to refer not to the biological material that is synthesized on a substrate or deposited on a slide, as described above, but to what has been referred to herein as the target. To avoid confusion, the term probe is used herein to refer to probes such as those synthesized according to the VLSIPS™ technology; the biological materials deposited or positioned so as to create spotted arrays; and materials synthesized, deposited, or positioned to form arrays according to other current or future technologies. Thus, microarrays formed in accordance with any of these technologies may be referred to generally and collectively hereafter for convenience as probe arrays. Moreover, the term probe is not limited to probes immobilized in array format. Rather, the functions and methods described herein may also be employed with respect to other parallel assay devices. For example, these functions and methods may be applied with respect to information obtained from labeled targets hybridized to probes immobilized on or in beads, optical fibers, or other substrates or media.

Probes typically are able to detect the expression of corresponding genes or EST's by detecting the presence or abundance of mRNA transcripts present in the target. This detection may, in turn, be accomplished by detecting labeled cRNA that is derived from cDNA derived from the mRNA in the target. In general, a group of probes, sometimes referred to as a probe set, contains sub-sequences in unique regions of the transcripts and does not correspond to a full gene sequence. Further details regarding the design and use of probes are provided in U.S. Pat. No. 6,188,783; in PCT Application Serial No. PCT/US01/02316, filed Jan. 24, 2001; and in U.S. patent applications Ser. No. 09/721,042, filed on Nov. 21, 2000, U.S. Ser. No. 09/718,295, filed on Nov. 21, 2000, U.S. Ser. No. 09/745,965, filed on Dec. 21, 2000, and U.S. Ser. No. 09/764,324, filed on Jan. 16, 2001, all of which patents and patent applications are hereby incorporated herein by reference in their entireties for all purposes.

Scanners 170: Labeled targets in hybridized probe arrays 172 may be detected using various commercial devices, sometimes referred to as scanners. Illustrative devices are shown in FIG. 1 as scanners 170A and 170B. Scanners image the targets by detecting fluorescent or other emissions from the labels, or by detecting transmitted, reflected, or scattered radiation. These processes are generally and collectively referred to hereafter for convenience simply as involving the detection of emissions. Various detection schemes are employed depending on the type of emissions and other factors. A typical scheme employs optical and other elements to provide excitation light and to selectively collect the emissions. Also generally included are various light-detector systems employing photodiodes, charge-coupled devices, photomultiplier tubes, or similar devices to register the collected emissions. For example, a scanning system for use with a fluorescent label is described in U.S. Pat. No. 5,143,854, incorporated by reference above. Other scanners or scanning systems are described in U.S. Pat. Nos. 5,578,832; 5,631,734; 5,834,758; 5,936,324; 5,981,956; 6,025,601; 6,141,096; 6,185,030; and 6,201,639, and in PCT Application PCT/US99/06097 (published as WO 99/47964); and in U.S. patent application Ser. Nos. 09/682,837 filed Oct. 23, 2001, U.S. patent application Ser. Nos. 09/683,216 filed Dec. 3, 2001, and U.S. patent application Ser. Nos. 09/683,217 filed Dec. 3, 2001, 09/683,219 filed Dec. 3, 2001, each of which patent and patent application is hereby incorporated by reference in its entirety for all purposes.

Figure 2:
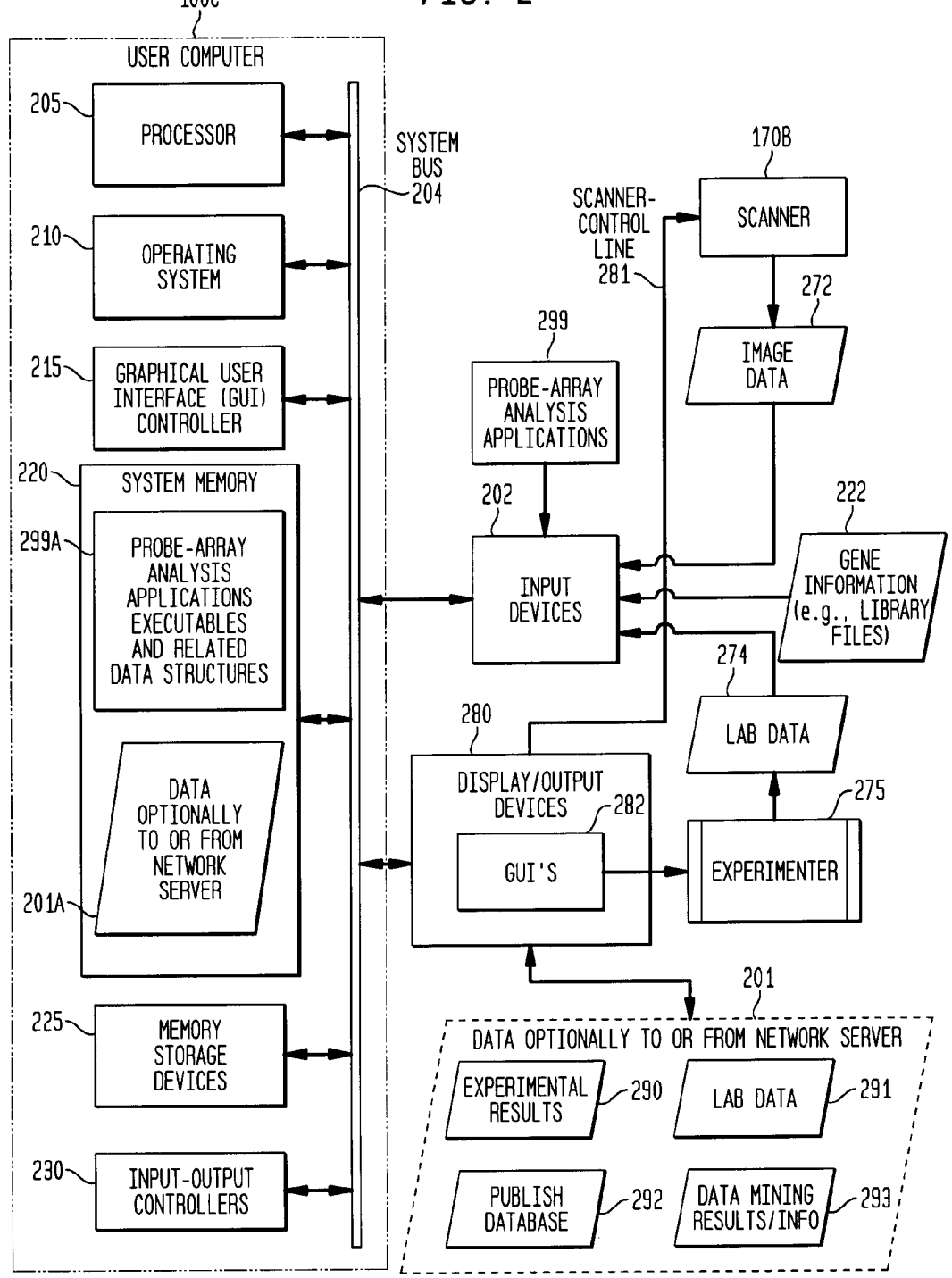
FIG. 2 is a functional block diagram of one embodiment of a user computer that optionally may be part of the computer network system of FIG. 1 or may operate in a stand-alone mode, and upon which a data manager application in accordance with aspects of the present invention may be executed.

As shown in FIG. 2, illustrative scanner 170B provides image data 272 representing the intensities (and possibly other characteristics, such as color) of the detected emissions, as well as the locations on the substrate where the emissions were detected. Typically, image data 272 includes intensity and location information corresponding to elemental sub-areas of the scanned substrate. The term elemental in this context means that the intensities, and/or other characteristics, of the emissions from this area each are represented by a single value. When displayed as an image for viewing or processing, elemental picture elements, or pixels, often represent this information. Thus, for example, a pixel may have a single value representing the intensity of the elemental sub-area of the substrate from which the emissions were scanned. The pixel may also have another value representing another characteristic, such as color. Two examples of image data are data files in the form *.dat or *.tif as generated respectively by Affymetrix® Microarray Suite based on images scanned from GeneChip® arrays, and Affymetrix® Jaguar™ software based on images scanned from spotted arrays. More details are provided in U.S. Provisional Patent Applications Nos. 60/220,645, and 60/226,999, which are hereby incorporated by reference herein in their entireties for all purposes.

User Computers 100: FIG. 2 is a functional block diagram of illustrative user computer 100C that, as noted, optionally may be coupled to network 125 or may operate in a stand-alone mode. Computer 100C typically is a workstation-class computer, may also be any other type of computer platform such as a personal computer, a server, or any other present or future computer. Computer 100C typically includes known components such as a processor 205, an operating system 210, a system memory 220, memory storage devices 225, and input-output controllers 230. It will be understood by those skilled in the relevant art that there are many possible configurations of the components of computer 100 and that some components that may typically be included in computer 100 are not shown, such as cache memory, a data backup unit, and many other devices. Processor 205 may be a commercially available processor such as a Pentium® processor made by Intel Corporation, a SPARC® processor made by Sun Microsystems, or it may be one of other processors that are or will become available. Processor 205 executes operating system 210 that may be, for example, a Windows® operating system from the Microsoft Corporation; a Unix® or Linux operating system available from many vendors; another or a future operating system; or some combination thereof. Operating system 210 interfaces with firmware and hardware in a well-known manner, and facilitates processor 205 in coordinating and executing the functions of various computer programs that may be written in a variety of programming languages. Operating system 210, typically in cooperation with processor 205, coordinates and executes functions of the other components of computer 100C. Operating system 210 also provides scheduling, input-output control, file and data management, memory management, and communication control and related services, all in accordance with known techniques.

System memory 220 may be any of a variety of known or future memory storage devices. Examples include any commonly available random access memory (RAM), magnetic medium such as a resident hard disk or tape, an optical medium such as a read and write compact disc, or other memory storage device. Memory storage devices 225 may be any of a variety of known or future devices, including a compact disk drive, a tape drive, a removable or internal hard disk drive, or a diskette drive. Such types of memory storage devices 225 typically read from, and/or write to, a program storage medium (not shown) such as, respectively, a compact disk, magnetic tape, removable or internal hard disk, or floppy diskette. Any of these program storage media, or others now in use or that may later be developed, may be considered a computer program product. As will be appreciated, these program storage media typically store a computer software program and/or data. Computer software programs, also called computer control logic, typically are stored in system memory and/or the program storage medium used in conjunction with memory storage devices 225.

In some embodiments, a computer program product is described comprising a computer usable medium having control logic (computer software program, including program code) stored therein. The control logic, when executed by processor 205, causes processor 205 to perform the functions of data manager 425 and other software applications described herein. In other embodiments, some functions may be implemented primarily in hardware using, for example, a hardware state machine. Implementation of the hardware state machine so as to perform the functions of data manager 425 described herein will be apparent to those skilled in the relevant arts.

Input-output controllers 230 could include any of a variety of known devices for accepting and processing information from a user, whether a human or a machine, whether local or remote. Such devices include, for example, modem cards, network interface cards, sound cards, or other types of controllers for any of a variety of known input devices 202. Output controllers of input-output controllers 230 could include controllers for any of a variety of known display devices 280 for presenting information to a user, whether a human or a machine, whether local or remote. If one of display devices 280 provides visual information, this information typically may be logically and/or physically organized as an array of picture elements, sometimes referred to as pixels. Graphical user interface (GUI) controller 215 may comprise any of a variety of known or future software programs for providing graphical input and output interfaces between computer 100C and experimenter 275, and for processing inputs from experimenter 275 (hereafter sometimes referred to as user inputs or user selections). In the illustrated embodiment, the functional elements of computer 100C communicate with each other via system bus 204. Some of these communications may be accomplished in alternative embodiments using network or other types of remote communications, such as when the functions of one or more of probe-array analysis applications 299 are distributed over or among others of user computers 100 and/or server computer 120.

As will be evident to those skilled in the relevant art, applications 299, if implemented in software, may be loaded into system memory 220 and/or memory storage device 225 through one of input devices 202. All or portions of applications 299 may also reside in a read-only memory or similar device of memory storage device 225, such devices not requiring that applications 299 first be loaded through input devices 202. It will be understood by those skilled in the relevant art that applications 299, or portions of any of them, may be transferred by processor 205 in a known manner among system memory 220, memory storage device 225, or cache memory (not shown) as advantageous for execution. Thus, applications and data structures may be shown for convenience in the illustrated embodiment as located in system memory 220 but, in some implementations, may be located in or shifted among other memory devices as convenient for data storage, data retrieval, and/or execution. In some implementations, the functional elements of executables of data manager 425 (e.g., aspects of executables 299A) comprise sets of software instructions that cause the described functions to be performed. These software instructions may be programmed in any programming language. Executables of data manager 425 may therefore be referred to as a set of data management instructions, and the functional elements of data manager 425 may similarly be described, for example, as sets of publish database generator instructions, as represented by generator 620.

As indicated by scanner-control line 281 of FIG. 2, computer 100C may control aspects of the operations of scanner 170B, as well as of other instruments involved in probe-array experiments, such as fluidics stations (not shown). These control functions may be carried out by the execution of aspects of appropriate software programs, such as Affymetrix® Microarray Suite (for scanning Affymetrix® GeneChip® arrays) or Affymetrix® Jaguar™ software (for scanning spotted arrays). In other implementations, scanner 170B may be controlled by these or other applications executing on server 120.

Figure 3:
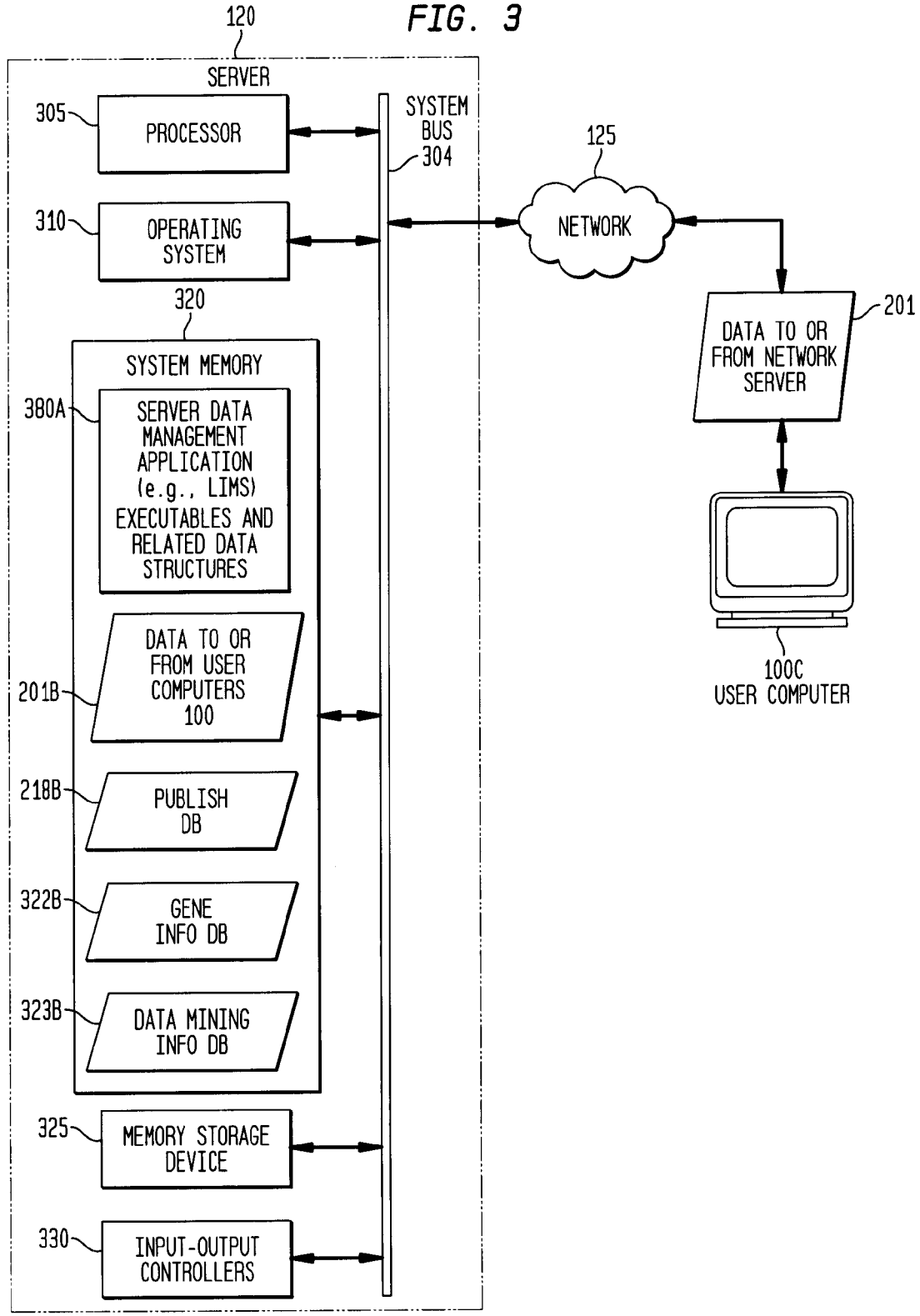
FIG. 3 is a functional block diagram of one embodiment of a server computer suitable for use with the computer network system of FIG. 1.

Server 120: FIG. 3 is a functional block diagram of an illustrative implementation of server 125 as coupled over network 125 to user computer 100C. Typically, server 120 is a network-server class of computer designed for servicing a number of workstations or other computer platforms over a network. However, server 120 may be any of a variety of types of general-purpose computers such as a personal computer, workstation, main frame computer, or other computer platform now or later developed. Server 120 typically includes known components such as processor 305, operating system 310, system memory 320, memory storage devices 325, and input-output controllers 330, corresponding to known components of user computer 100C described above. It will be understood by those skilled in the relevant art that there are many possible configurations of the components of server 120 and that a great variety of known components typically are included in it, but are not shown, such as cache memory, a data backup unit, and many other devices. Similarly, many other hardware and associated software or firmware components that may be associated with the network server are not shown. For example, components to implement one or more firewalls to protect data and applications, uninterruptable power supplies, LAN switches, web-server routing software, and many other components may be used. Those of ordinary skill in the art will readily appreciate how these and other conventional components may be implemented.

The server's processor may include multiple processors; e.g., multiple Intel Xeon® 700 MHz. As further examples, the server processor may include one or more of a variety of other commercially available processors such as Pentium® processors from Intel, SPARC® processors made by Sun Microsystems, or other processors that are or will become available. Operating system 310 may be, for example, a Windows® operating system (such as Windows® 2000 with SP 1, Windows NT® 4.0 with SP6a) from the Microsoft Corporation; the Solaris operating system from Sun Microsystems, the Tru64 Unix from Compaq, other Unix® or Linux-type operating systems available from many vendors; another or a future operating system; or some combination thereof.

Probe Array Analysis Applications 299: One or more of probe-array analysis applications 299 may be executed either on user computers 100, server 120, or on one or more other computer platforms connected directly or indirectly (e.g., via another network, including the Internet or an intranet) to network 125. Also, some implementations of applications 299, such as Affymetrix® Laboratory Information Management System (LIMS), may have components both on server 120 and on user computers 100. Aspects of a particular implementation of a LIMS application are described in U.S. patent application Ser. No. 09/683,912, which is hereby incorporated herein by reference in its entirety for all purposes.

In the illustrated implementation of FIG. 2, some of applications 299 are executed on user computer 100C. These applications 299 may include a variety of known or future image processing, data processing, and/or data management applications related to the analysis and management of probe-array experiments. Examples of applications 299 are Affymetrix® Data Mining Tool, Affymetrix® MicroDB, Affymetrix® Microarray Suite, Affymetrix® Jaguar™ software, or any combination thereof. Aspects of a particular implementations of such software are described in U.S. Provisional Patent Applications No. 60/274,986, which is hereby incorporated herein by reference in its entirety for all purposes. Applications 299, as loaded into system memory 220, are shown in FIG. 2 as probe-array analysis applications executables 299A.

FIG. 4 is a functional block diagram showing in greater detail how probe-array analysis applications executables 299A may operate to process lab data 274, gene information 222, and/or image data 272. Lab data 274 may include information input by experimenter 275 and/or automated data input devices or programs (not shown) related to the design or conduct of experiments on probe arrays 172B. For instance, experimenter 275 may enter the names and dates of experiments, the types of fluorescent dyes used as labels, protocols followed, scanning parameters employed, the equipment and experimental protocols employed, name of the experimenter, and numerous other attributes of experiments.

Gene information 222 may be in the form, for example, of library files provided on a CD-ROM or other memory storage device, or downloaded over network 125. Gene information 222 provides information about genes or EST's represented by probe sets or probes of probe arrays 172B. This information may include, for example, probe array design characteristics such as details regarding the sequences and locations of probes and controls, scanning parameters, default analysis parameters, and annotations and literature references related to the represented genes or ESTs.

Image data 272 is generated by scanner 170B and provided to computer 100C. Two non-limiting examples of image data are data files in the form *.dat or *.tif as generated respectively by Affymetrix® Microarray Suite based on images scanned from GeneChip® arrays, and Affymetrix® Jaguar™ software based on images scanned from spotted arrays. In alternative implementations, these image data may be provided to server 120 for processing.

In the illustrated implementation of FIG. 4, image data 272 is operated upon by probe-array analysis applications executables 299A to generate experimental results 415. Non-limiting examples of experimental results 415 are so-called cell intensity files (*.cel) and chip files (*.chp) generated by Affymetrix® Microarray Suite, and spot files (*.spt) generated by Affymetrix® Jaguar™ software.

In the non-limiting example in which image data 272 is derived from a GeneChip® probe array, applications 410 (e.g., Affymetrix® Microarray Suite) generates from that data a cell intensity file. This file contains, for each probe scanned by scanner 170B, a single value representative of the intensities of pixels measured by scanner 170B for that probe. Thus, this value is a measure of the abundance of cRNA's present in the target that hybridized to the corresponding probe. Many such cRNA's may be present in each probe, as a probe on a GeneChip® probe array may include, for example, millions of oligonucleotides designed to detect the cRNA's. As noted, another file illustratively assumed to be generated by applications 410 is a chip file. The chip file is derived from analysis of the cell file combined in some cases with information derived from lab data 274 and gene information 222. The resulting data stored in the chip file includes degrees of hybridization, absolute and/or differential (over two or more experiments) expression, genotype comparisons, detection of polymorphisms and mutations, and other analytical results.

In another example, in which image data 272 is derived from a spotted probe array, applications 410 (e.g., Affymetrix® Jaguar™ software) generates a spot file including the intensities of labeled targets that hybridized to probes in the array. Further details regarding cell files, chip files, and spot files are provided in U.S. Provisional Patent Application Nos. 60/220,645 and 60/226,999, incorporated by reference above. As will be appreciated by those skilled in the relevant art, the preceding and following descriptions of files generated by executables 299A are exemplary only, and the data described, and other data, may be processed, combined, arranged, and/or presented in many other ways. For convenience, the term file often is used herein to refer to data generated or used by executables 299A and executable counterparts of other applications, but it will be understood that any of a variety of alternative techniques known in the relevant art for storing, conveying, and/or manipulating data may be employed.

As noted, applications 410 may apply some of this data in the generation of experimental results 415. For example, information about the dyes may be incorporated into determinations of relative expression. Other (or all) aspects of lab data 274, such as the name of the experimenter, may be processed by applications 410 or may simply be preserved and stored in files or other data structures such as illustrative lab data 291. These and other data are collectively shown as data 201 and, as shown in FIG. 2, may be provided over network 125 for processing and/or storage in server 120.

Figure 5:
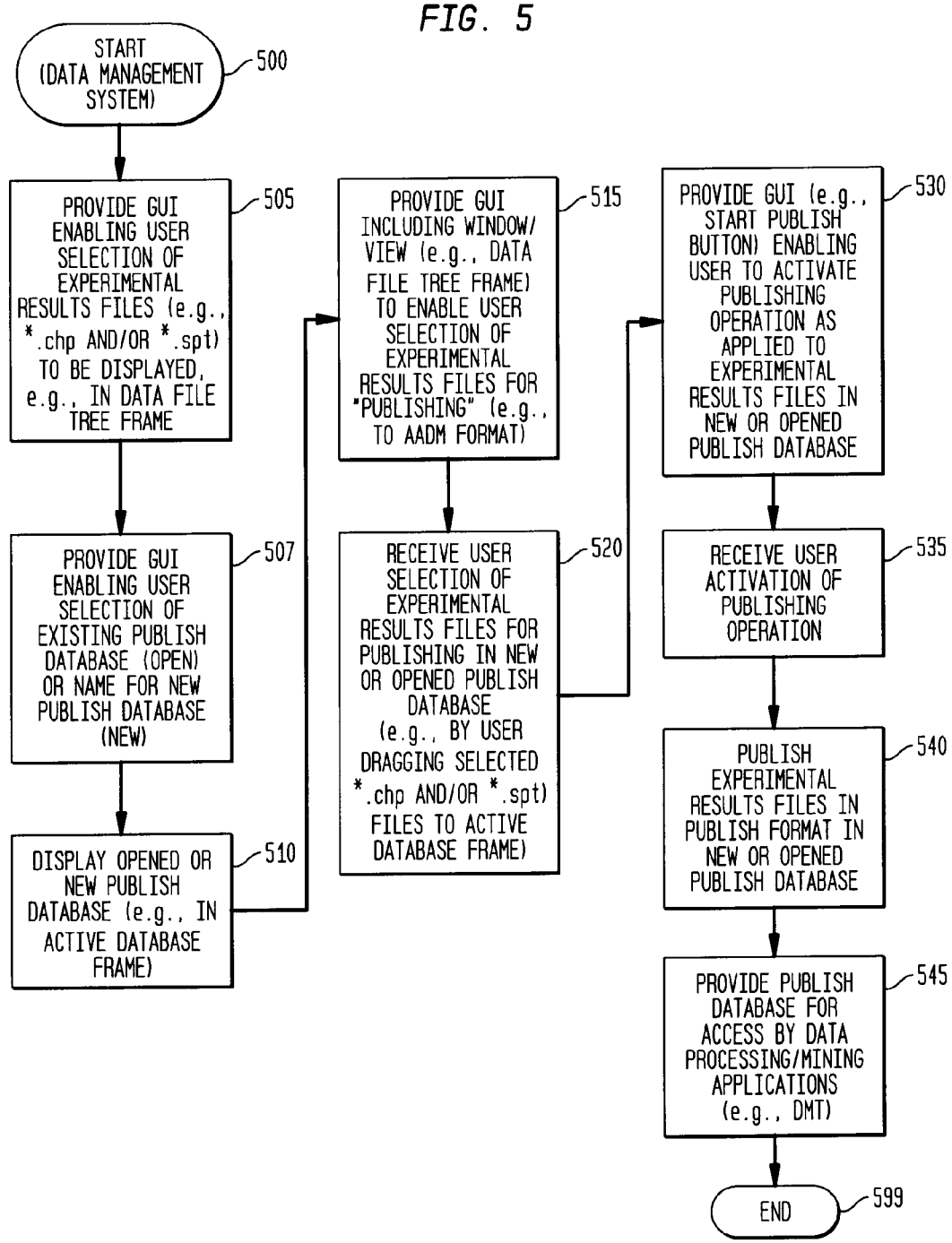
FIG. 5 is a flow diagram of one embodiment of data-management method steps in accordance with aspects of a data management application of the software applications of FIG. 4.
Figure 6:
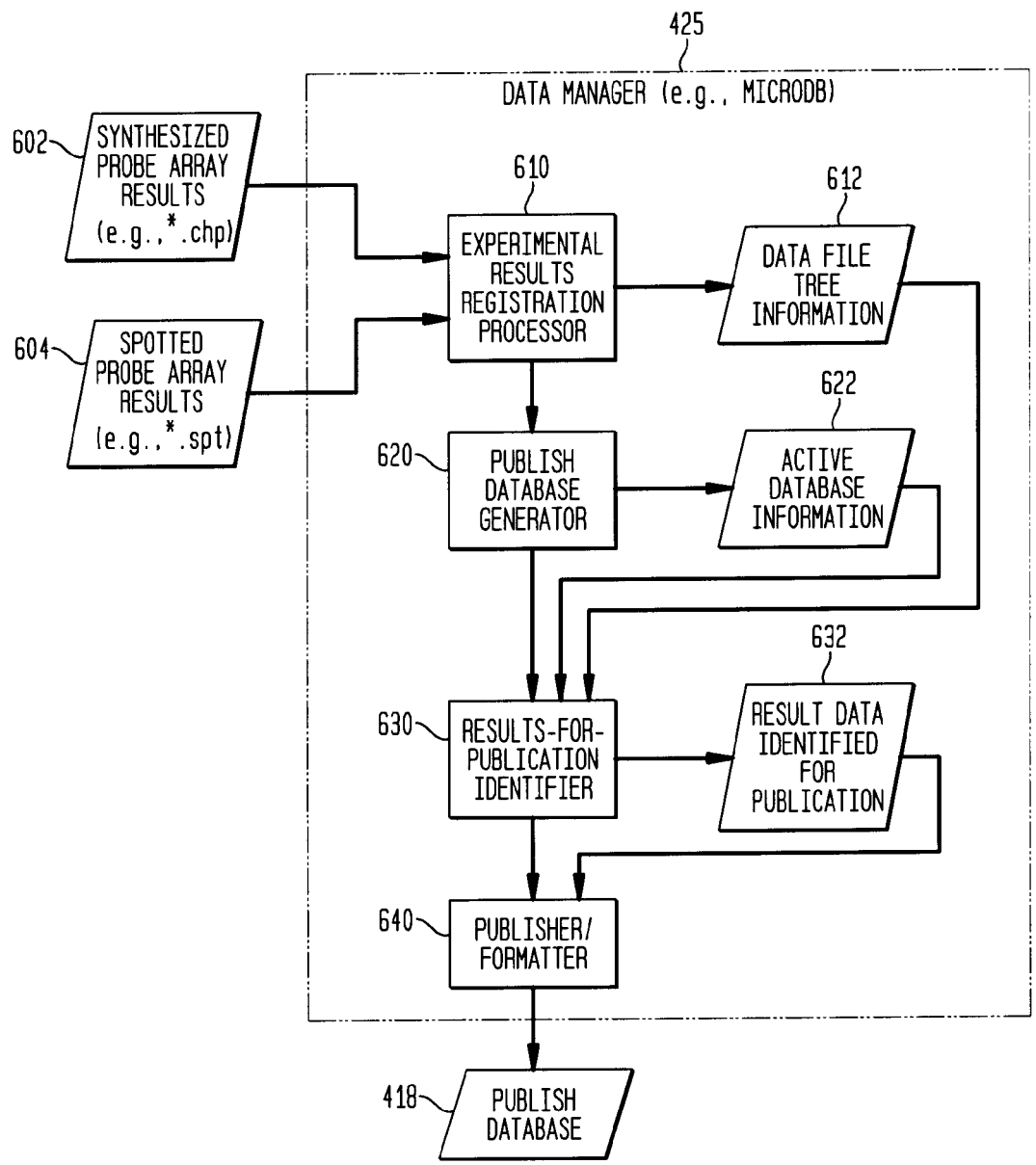
FIG. 6 is a functional block diagram of one implementation of a data manager application such as may be included in the probe-array analysis applications executables and related data structures of FIG. 3.
Figure 10:
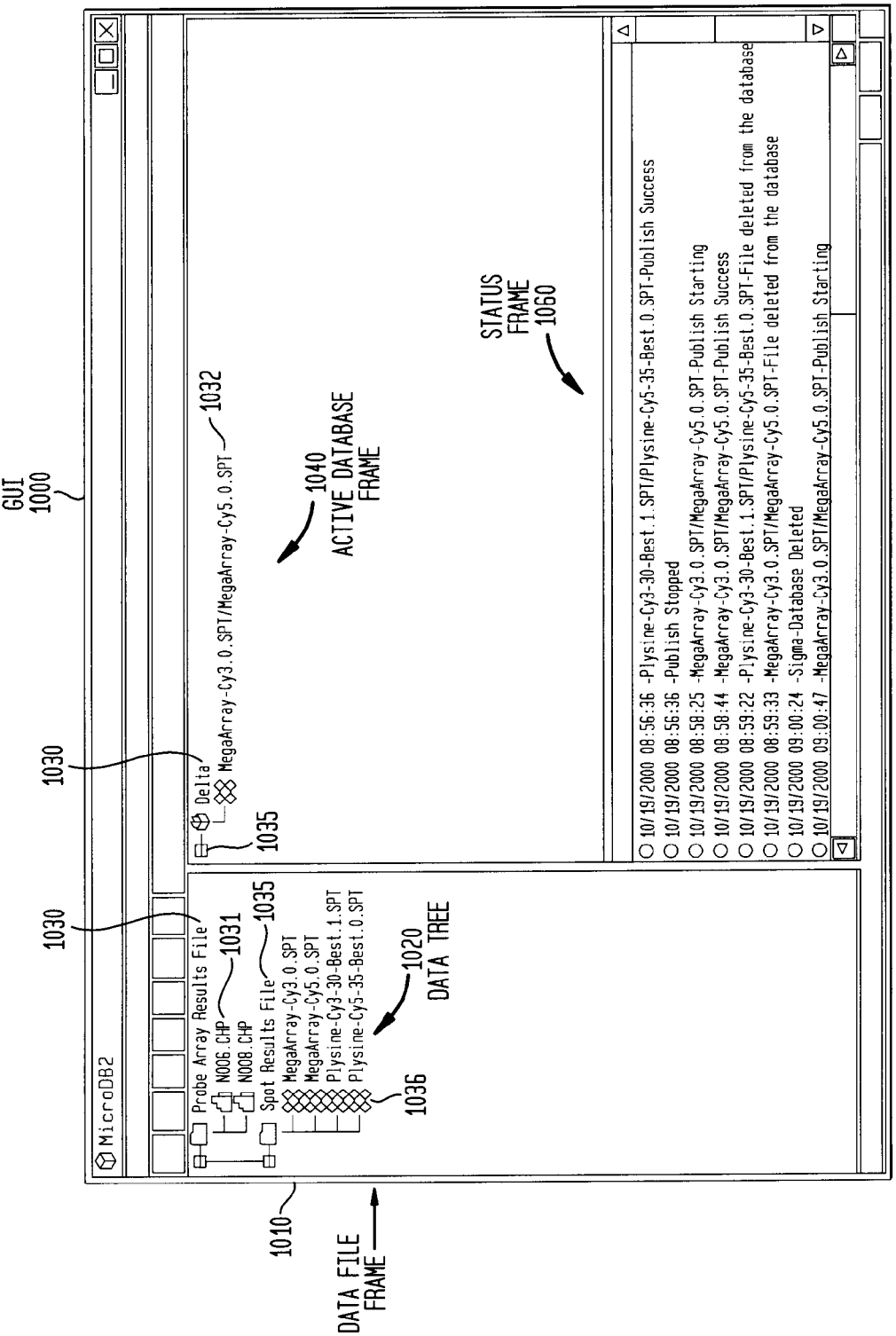
FIG. 10 is a graphical representation of one embodiment of a graphical user interface suitable for use with the data manager application of FIG. 6.

Data Manager 425: FIG. 5 is a flow diagram of data-management method steps in accordance with an illustrative implementation of data manager 425. FIG. 6 is a functional block diagram of one implementation of data manager 425. FIG. 10 is a graphical representation of an illustrative graphical user interface (GUI) that may be employed by data manager 425 to present data to and obtain input from a user. Data manager 425 (as well as data mining tool 420 and other software applications referred to herein) may be implemented using C++, Microsoft® Visual C++, Java, Visual Basic, any other high-level or low-level programming language, or any combination thereof. In alternative implementations, some or all of the functions described herein as performed by data manager 425 may be provided by server data management application executables 380A.

As shown in FIG. 6, data manager 425 of the illustrated implementation includes experimental results registration processor 610 that registers synthesized probe array results (e.g., from *.chp files), and spotted probe array results (e.g., from *.spt files) for publishing. The word registration and its grammatical variants refers in this context to identifying probe array results that may further be selected for publishing. As indicated by method step 505 of FIG. 5, the registration operation may be facilitated by providing a GUI suitable for enabling a user (e.g., experimenter 275) to select both types of probe array result files for registration. The result of the user selection may be to display the selected probe array results in a data file window frame of a window-type GUI. Illustrative data file frame 1010 of GUI 1000 is shown in FIG. 10. The information used to display frame 1010 may be stored in an appropriate data structure, such as data file tree information 612. Frame 1010 includes data tree 1020 having both branch 1030 for displaying synthesized probe array results and branch 1035 for displaying spotted probe array results. In these branches are displayed graphical elements representing probe array results selected by experimenter 275 for registration. For example, an icon plus description (element 1031) represents selected synthesized probe array results and another type of icon plus description (element 1036) represents selected spotted probe array results. Experimenter 275 may select one or more of these graphical elements from data tree 1020 for publication (as indicated by step 515).

Data manager 425 of the illustrated implementation also includes a publish database generator 620 that enables experimenter 275 to select an existing or new database to be the publish database (see step 507). The selected database may be represented in active database frame 1040 (see step 510) of GUI 1000 as, for example, graphical element 1030 at the root of tree structure 1035. The information used to display the user-selected active database in frame 1040 may be stored in an appropriate data structure, such as active database information 622. By selecting and dragging from frame 1020 to frame 1040, or any of a variety of other known techniques, experimenter 275 may indicate that one or more of the probe array result files shown in frame 1020 are selected for publishing (see step 520). A graphical element representing this file, e.g., element 1032, may then be added by results-for-publication identifier 630 to tree structure 1035 to indicate that the corresponding file has been selected for publication. The information used to display the selected files in the tree of frame 1040 may be stored in an appropriate data structure, such as result data identified for publication 632. More generally, data manager 425 includes results-for-publication identifier 630 that identifies synthesized probe array results and/or spotted probe array results for publishing.

Data manager 425 also, in this implementation, includes publisher/formatter 640 that publishes the user-selected synthesized probe array results and/or the spotted probe array results to a publish database (see steps 530, 535, 540, and 545), represented in FIGS. 4 and 6 as publish database 418. Typically, publish database 418 is a relational database.

Database 418 of the illustrated implementation is designed in accordance with an integrated database schema, such as the Affymetrix® Analysis Data Model (AADM) schema, shown schematically in FIG. 9. This schema describes a relational database architecture that may be used as a persistent store for gene expression and mapping data produced, for example, by the Affymetrix® Microarray Suite Software after GeneChip® array analysis. This data model can also be used for storing spotted array analysis results produced by, for example, the Affymetrix® Jaguar™ software. Subsequently, the data from either the GeneChip or spotted array platforms can be analyzed and mined within this data architecture, such as by data mining tool 420.

Figure 7:
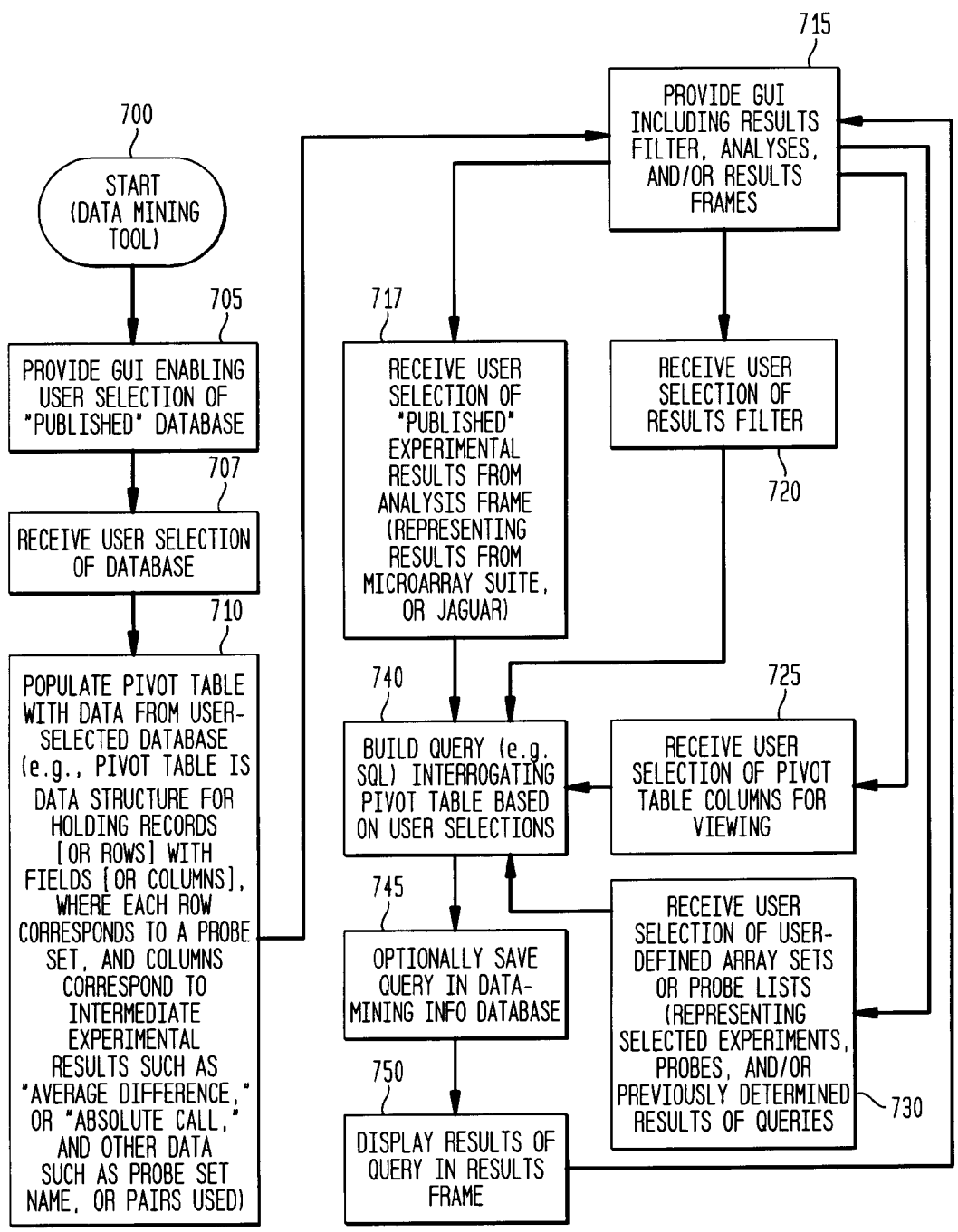
FIG. 7 is a flow diagram of one embodiment of data-mining-tool method steps that may be exercised in relation to published databases generated in accordance with aspects of the present invention.
Figure 9A:
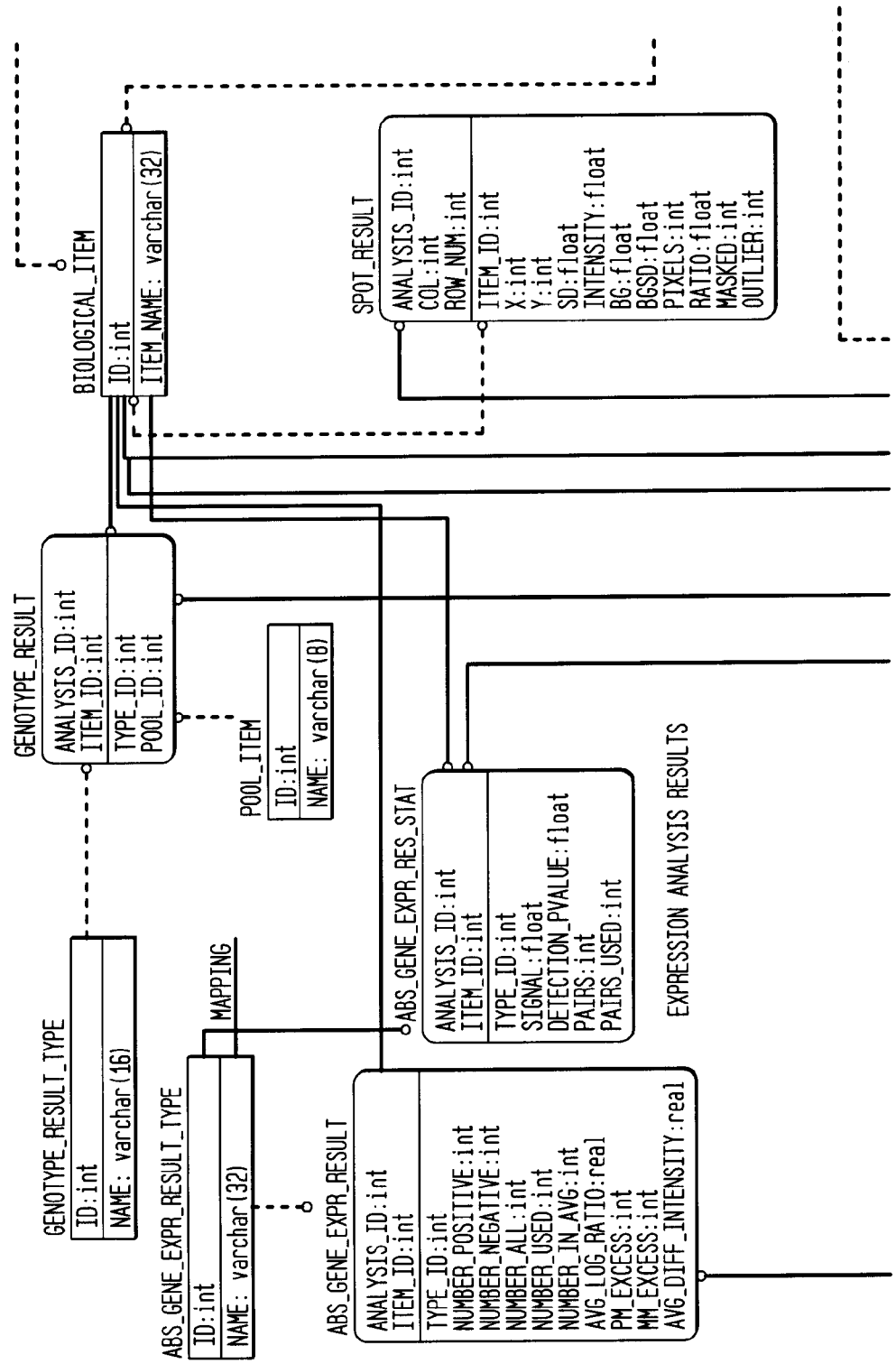
FIG. 9 is an entity-relation diagram of database objects of one embodiment of a database as published in accordance with aspects of the present invention.
Figure 9B:
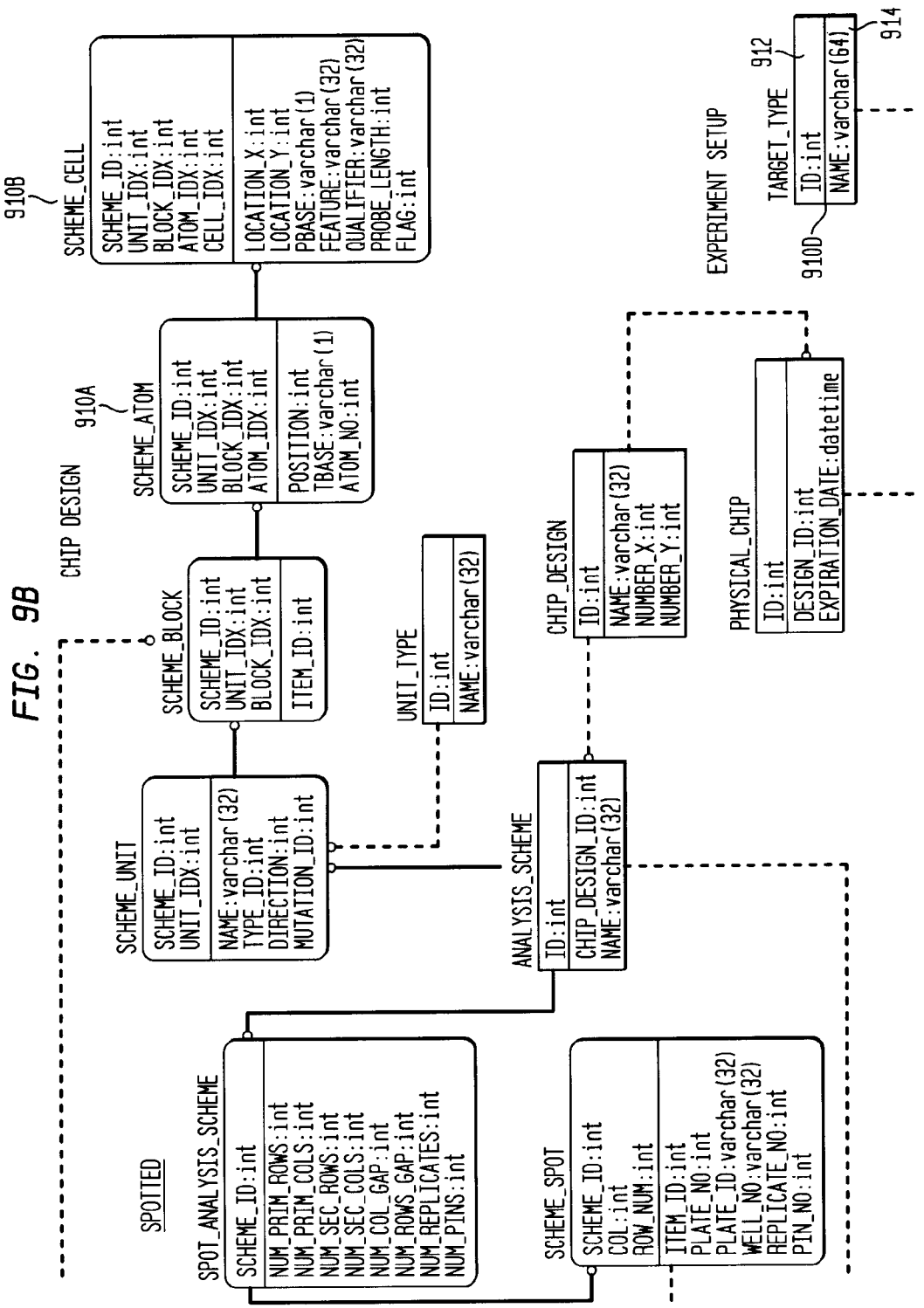
Figure 9C:
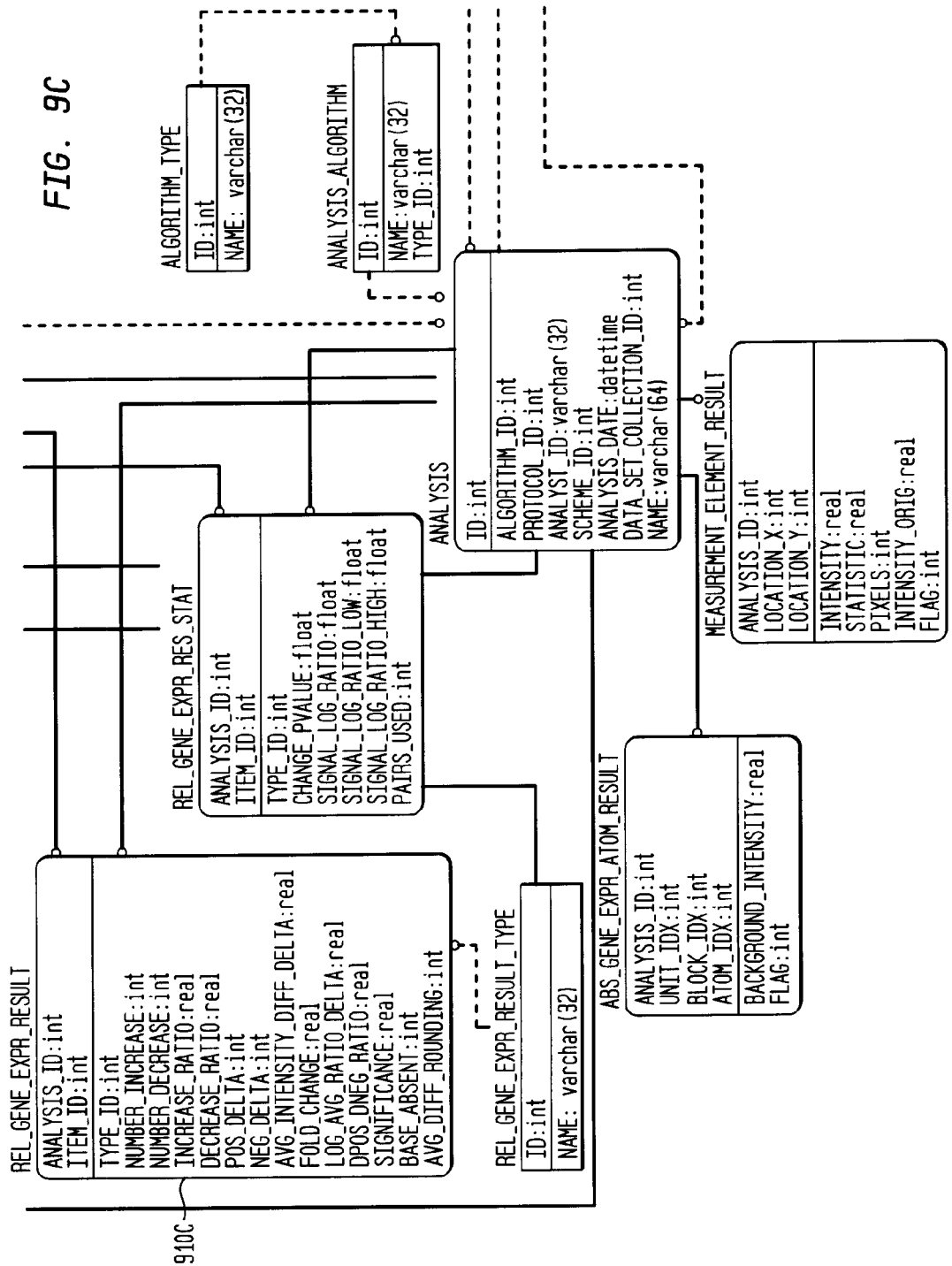
Figure 9D:
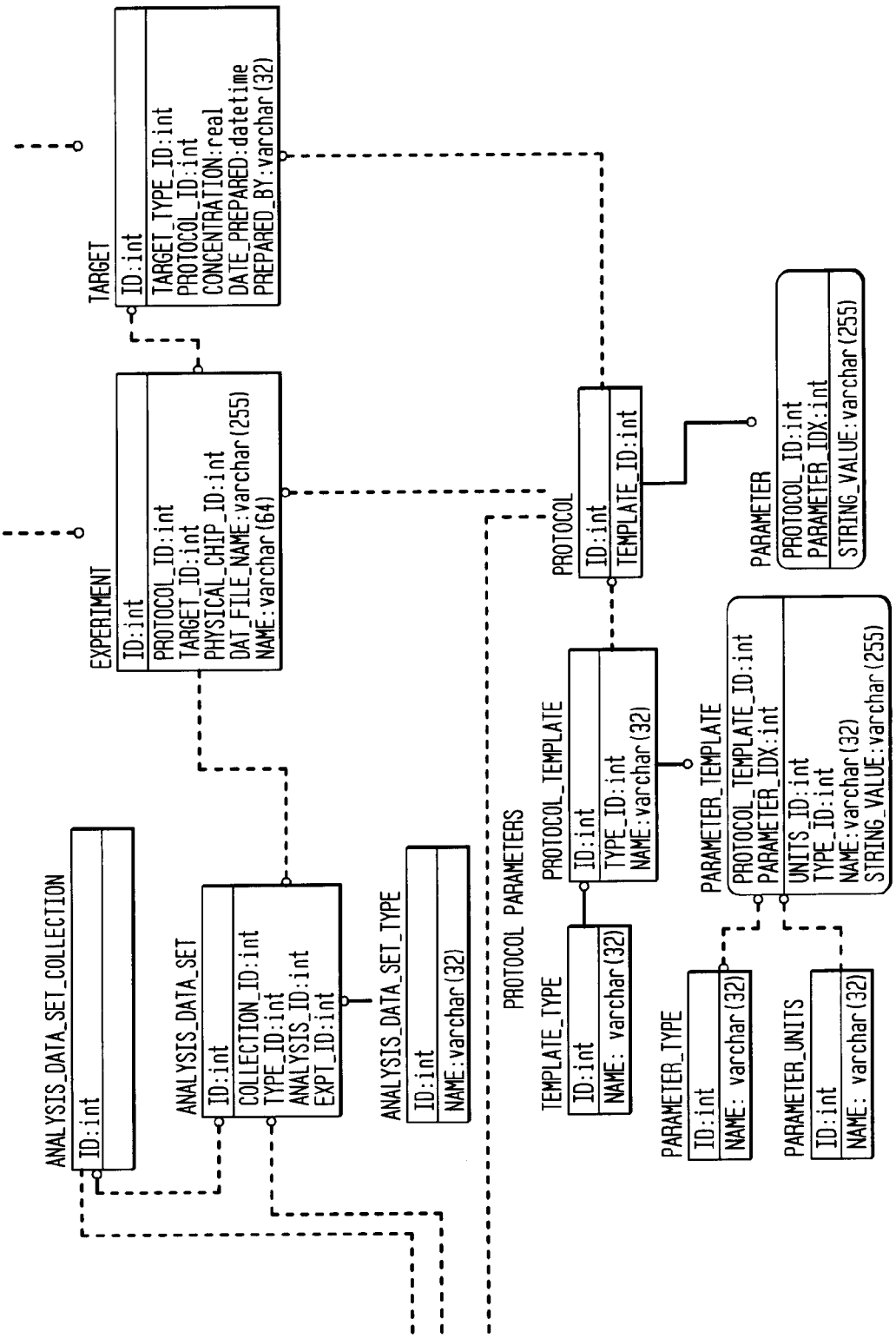
Figure 11:
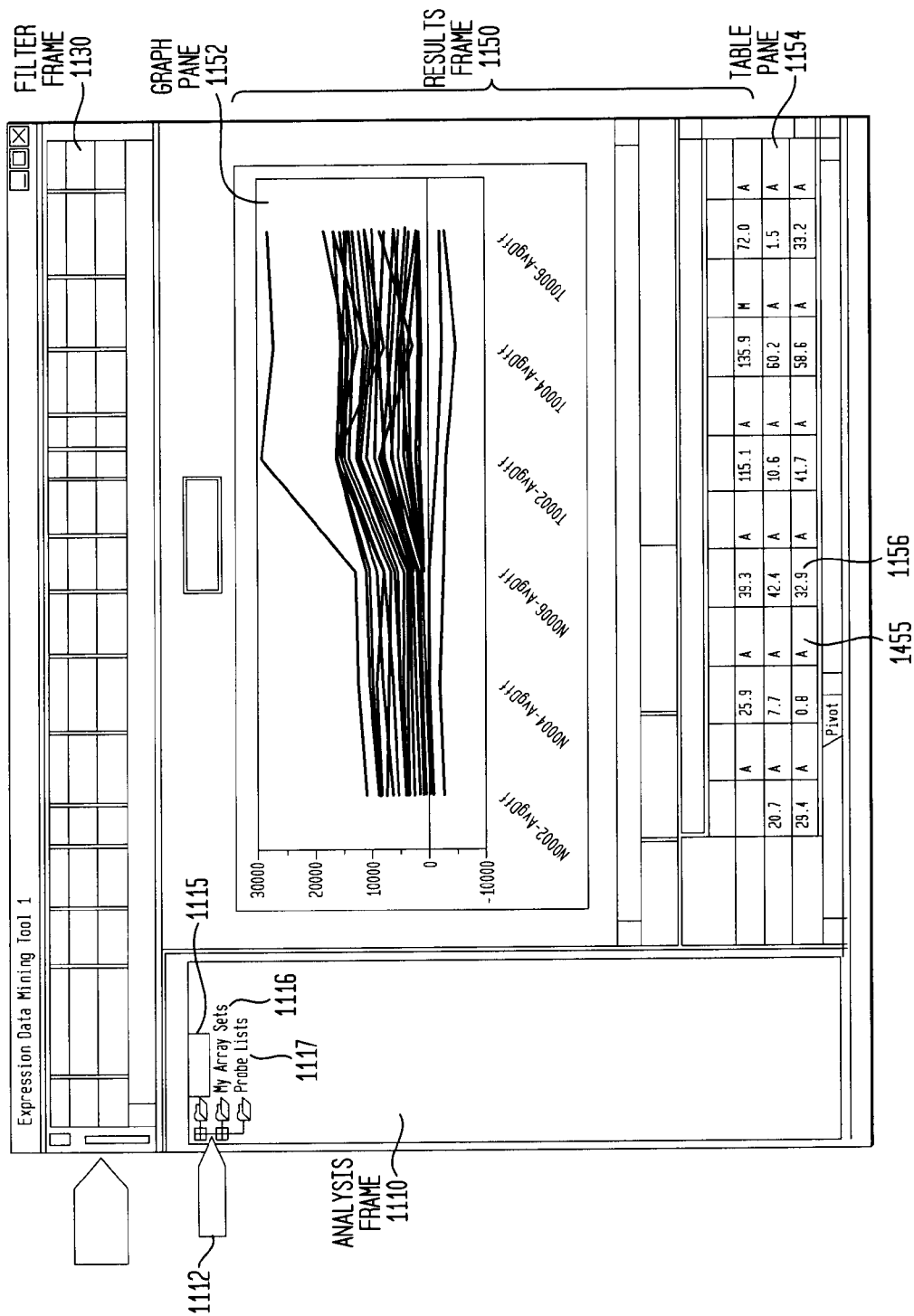
FIG. 11 is a graphical representation of one embodiment of a graphical user interface suitable for use with the data-mining-tool application of FIG. 8.

Data Mining Tool 420: FIG. 7 is a flow diagram of data-mining method steps in accordance with an illustrative implementation of data mining tool 420. FIG. 8 is a functional block diagram of one implementation of data mining tool 420. FIG. 11 is a graphical representation of an illustrative GUI that may be employed by data mining tool 420 to present data to and obtain input from a user. In the present implementation, data mining tool 420 operates on publish database 418 published by data manager 425. In some of a variety of other implementations, data mining tool 420 may operate on a publish database published by server data management applications, such as a Laboratory Information Management System application, executed on server 120. Also, data mining tool 420 in some implementations may operate directly on experimental results from probe-array experiments without publication in a publish format. A publish format typically is provided to facilitate and/or standardize data transfers to and from a data mining tool, but this formatting is not necessarily a feature of some implementations.

As shown in FIG. 8, data mining tool 420 of the illustrated implementation includes published database registration processor 810 that enables a user to register a published database for data mining. In this example, this operation may be accomplished by experimenter 275 selecting publish database 418 from a list, tree, other graphical representation of files or data structures, or in accordance with other known techniques (see method steps 705 and 707). For example, analysis frame 1110 of GUI 1100 of FIG. 11 may display a tree including branch 1115 that may be expanded according to known techniques to display graphical elements representing published results from probe array experiments in a publish database. Data from the user-selected publish database may be stored for convenience of execution in registered published database 812, or the data may be left in publish database 418 for access by other elements of tool 420. One such other element of data mining tool 420 in the present implementation is pivot table populator 820 that extracts data from registered published database 812 (or, alternatively, directly from publish database 418). Populator 820 places this data in fully populated pivot table 822 (see step 710). Data mining tool 420 of the illustrative implementation provides one or more GUI's to facilitate the operations of results filter 830, experiment selector 840, array set or probe list selector 850 and/or selective column viewer 860 (see step 715).

Results filter 830 processes user-selected filter criteria (see step 717) that it provides to query builder 870 so that it may build queries (see step 740) in an appropriate language, such as SQL, to be applied to pivot table 822. These filter criteria may include, for example, selection of published experimental result files from synthesized and/or spotted probe arrays, as displayed, for example, in the analyses branch 1115 of data tree structure 1112. Experiment selector 840, based on user selection of particular experiments from analysis frame 1110, may similarly provide query builder 870 with a selection of experiments so that query builder 870 may query table 822 according to those criteria. Similarly, array set or probe list selector 850, based, for example, on user selections from expanded my-array-sets 1116 or probe-list 1117 branches of data tree 1112 in analysis frame 1110 (see step 730). In accordance with the operations of selective column viewer 860, a user may also select particular columns of pivot table 822 for display, such as columns 1155 or 1156 of table pane 1154 of results frame 1150 of the example of FIG. 11. The user-selected columns similarly are provided to query builder 870 for building of appropriate queries to pivot table 822 (see method step 725). Also, various filters may be applied by a user employing, for example, query building techniques employed through filter frame 1130 of GUI 1100 (see step 720).

Query builder 870 builds queries according to the various filters and criteria specified by experimenter 275 and uses them to interrogate table 822 (see step 740). Query manager 875 receives the response to the queries and optionally stores the result in a data structure (such as table 872) and/or simply provides the data to results tables and graphs builder 880 to build a display. For example, data returned from a query may be displayed in table pane 1154 of results frame 1150 of illustrative GUI 1100. Similarly, various graphs (such as histograms, scatter plots, series plots, and fold changes) may be built by builder 880 in accordance with known techniques by builder 880 and displayed in graph pane 1152 of results frame 1150 (see step 750). Also, query manager 875 may store frequently used queries, or others selected by the user or according to other criteria, for future reference and display to the user (see step 745). Such information may be stored, for example, in data-mining info database 422.

Other details regarding the operations of data mining tool 420 are provided in U.S. Provisional Patent Applications Nos. 60/312,256 and 60/274,986, and in U.S. patent application Ser. No. 09/683,980, titled "System, Method, and User Interface for Mining of Genomic Data," filed concurrently herewith, all of which are hereby incorporated herein by reference in their entireties for all purposes.

Server Data Management Application Executables 380A: Various software applications may be loaded into server 120 in accordance with known techniques. One such application used to manage experimental information from a network of experimenters is often referred to as a laboratory information management system (LIMS) application, as noted above. The executable version of such an application is shown in FIG. 3 as server data management application executables 380A. Full database functionality is intended to provide a data streaming solution and a single infrastructure to manage information from probe array experiments. Application 380 provides a database storage and retrieval system for accessing and manipulating system data. The database server provides an automated and integrated data management environment for the end user. All process data, raw data and derived data may, in some implementations, be stored as elements of the database, providing an alternative to a file-based storage mechanism. A database back end may also provide integration of application 380 into a user's overall information system infrastructure. Data typically is accessible through standard interfaces and may be tracked, queried, archived, exported, imported and administered. Application 380, in a particular implementation, may support process tracking for a generic assay, may provide full Oracle® database management software or SQL Server solution, and may supports publishing of genotype and sequence data. In particular, application 380 of the illustrated example may provide processes for enabling sample definition, experiment setup, hybridization, scanning, grid alignment, cell intensity analysis, probe array analysis, publishing, and a variety of other functions related to experimental design and implementation. Application 380 may, in some implementations, support multiple experiments per sample definition via a re-queuing process, multiple hybridization and scan operations for a single experiment, data re-analysis, and publishing to more than one database. The process database, which may be implemented in any database systems such as an Oracle or SQL Server database management system, typically is supported by a COM communication layer to the process database. A gene-information database may also be provided to store chromosome and probe sequence information about the biological item on the probe array, and related information. Other features, as noted, may include publication of data in accordance with a database schema that typically is made public to enable third-party access and software interface development. For example, the AADM database schema provides for publication of Affymetrix® GeneChip® data with support for either an Oracle or SQL server database management system. Among other structures, tables are provided in the AADM implementation that provide support for genotype data.

In particular implementations, a LIMS security database implements a role-based security level that is integrated with Windows NT® user authentication security. The security database supports role definition, functional access within a role, and assignment of NT groups and users to those roles. A role is a collection of users who have a common set of access rights to probe array data. In an illustrative implementation, roles may be defined per server/database, and a role member may be a member of multiple roles. The software determines a user's access rights based on predetermined rules governing such rights as a function of role or other variable. A function is a pre-determined action that is common to all roles. Each role is defined by the functions it can and cannot perform. Functions explicitly describe the type of action that a member of the role can perform. The functions supported by a newly created role include, but are not limited to, read process data, delete process data, update process data, archive process data, assume ownership of process data, import process data, export process data, delete MDM data, create a AADM database, and maintaining roles. When a new user is added to a role, they typically have access privileges for their data and read only access privilege for other user data within the same role. All non-role members are denied all access privileges to role member's data. When application 380 of the illustrated implementation is installed, at least two roles may be created: administration and system user. The installer of the system software is added as a user to the administration role and a selected Windows NT® group is added as a user to the system user role.

In accordance with some implementations, a stand-alone application may be provided to enable user management capabilities. These capabilities include but are not limited to the following: AADM (or other schema) database creation, publish data deletion, process data deletion, taking ownership of process data, archiving and de-archiving of process data, data export, data import, role management, filter based find, managing expression analysis parameter sets, and managing sample and experiment attribution templates. Further details are provided in U.S. patent application Ser. No. 09/682,098, incorporated by reference above.

Having described various embodiments and implementations, it should be apparent to those skilled in the relevant art that the foregoing is illustrative only and not limiting, having been presented by way of example only. Many other schemes for distributing functions among the various functional elements of the illustrated embodiment are possible. The functions of any element may be carried out in various ways in alternative embodiments.

Also, the functions of several elements may, in alternative embodiments, be carried out by fewer, or a single, element. Similarly, in some embodiments, any functional element may perform fewer, or different, operations than those described with respect to the illustrated embodiment. Also, functional elements shown as distinct for purposes of illustration may be incorporated within other functional elements in a particular implementation. Also, the sequencing of functions or portions of functions generally may be altered. Certain functional elements, files, data structures, and so on, may be described in the illustrated embodiments as located in system memory of a particular computer. In other embodiments, however, they may be located on, or distributed across, computer systems or other platforms that are co-located and/or remote from each other. For example, any one or more of data files or data structures described as co-located on and local to a server or other computer may be located in a computer system or systems remote from the server. In addition, it will be understood by those skilled in the relevant art that control and data flows between and among functional elements and various data structures may vary in many ways from the control and data flows described above or in documents incorporated by reference herein. More particularly, intermediary functional elements may direct control or data flows, and the functions of various elements may be combined, divided, or otherwise rearranged to allow parallel processing or for other reasons. Also, intermediate data structures or files may be used and various described data structures or files may be combined or otherwise arranged. Numerous other embodiments, and modifications thereof, are contemplated as falling within the scope of the present invention as defined by appended claims and equivalents thereto.

What is claimed is:

1. A data manager for providing a publish database, comprising:

a results-for-publication identifier to identify at least one set of probe array results for publishing; and a publisher to publish the at least one set of probe array results and the at least one set of spotted probe array results as a first set of data in a publish database, said publish database is in a format or organized in accordance with a schema to facilitate access by data analysis applications, data mining applications, data reporting applications, other data processing applications or any combination thereof; wherein the at least one set of probe array results is in a first format and the publisher is constructed and arranged to publish the first set of data in a second format.

2. The data manager of claim 1, wherein:

the results-for-publication identifier identifies the at least one set of probe array results based, at least in part, on one or more user selections.

3. The data manager of claim 1, wherein:

the first set of data is organized in accordance with an integrated database schema.

4. The data manager of claim 3, wherein:

the integrated database schema includes all or part of an AADM schema.

5. The data manager of claim 1, wherein:

the publish database is a relational database.

6. The data manager of claim 1, wherein:

the publisher stores the publish database in a memory unit of a computer; and each of the first set of data in the publish database is addressable from a common reference address of the memory unit.

7. The data manager of claim 1, wherein:

the publisher stores the publish database in a memory unit of a computer as one or more related files.

8. The data manager of claim 1, further comprising:

an experimental results registration processor to register for publishing the at least one set of probe array results.

9. The data manager of claim 8, wherein:

the experimental results registration processor registers for publishing the at least one set of probe array results and the at least one set of spotted probe array based, at least in part, on one or more user selections.

10. A method for providing a publish database, comprising the steps of:

identifying at least one set of probe array results for publishing; and publishing the at least one set of probe array results as a first set of data in a publish database, said publish database is in a format or organized in accordance with a schema to facilitate access by data analysis applications, data mining applications, data reporting applications, other data processing applications or any combination thereof; wherein the at least one set of probe array results is in a first format and the publishing step includes publishing the first set of data in a second format.

11. The method of claim 10, wherein:

the identifying step includes identifying the at least one set of probe array results based, at least in part, on one or more user selections.

12. The method of claim 10, wherein:

the first set of data is organized in accordance with an integrated database schema.

13. The method of claim 10, wherein:

the publish database is a relational database.

14. The method of claim 10, wherein:

the publishing step includes storing the publish database in a memory unit of a computer; and each of the first set of data in the publish database is addressable from a common reference address of the memory unit.

15. The method of claim 10, wherein:

the publishing step includes storing the publish database in a memory unit of a computer as one or more related files.

16. The method of claim 10, further comprising the step of:

registering for publishing the at least one set of probe array results.

17. The method of claim 16, wherein:

the registering for publishing step includes publishing the at least one set of probe array results based, at least in part, on one or more user selections.

18. In a computer display system having a processor coupled to a display device such that data is displayed on the display device in a graphical user interface (GUI), a method for displaying the GUI and operating upon data displayed in or received from the GUI, comprising the steps of:

displaying a first frame in the GUI including a first set of graphical elements corresponding to at least one set of probe array results;

receiving a user, said publish database is in a format or organized in accordance with a schema to facilitate access by data analysis applications, data mining applications, data reporting applications, other data processing applications or any combination thereof; wherein the at least one set of probe array results is in a first format and the publisher is constructed and arranged to publish the first set of data in a second format selection of one or more of the first or second sets set of graphical elements for publication in a publish database;

displaying a second frame in the GUI including a second set of graphical elements corresponding to the publish database and, in relation thereto, a third set of one or more graphical elements corresponding to those of the first set of graphical elements selected by the user.

19. The method of claim 18, wherein:

the first frame includes a data file view wherein the first and second sets set of graphical elements are arranged in a first tree structure.

20. The method of claim 19, wherein:

the first set of graphical elements is arranged in a branch of the first tree structure.

21. The method of claim 18, wherein:

the first set of graphical elements corresponds to a probe array result file.

22. The method of claim 18, wherein:

the second frame includes an active database view wherein the second set of graphical elements is associated with a root of a tree structure and the third set of one or more graphical elements corresponding to those of the first set of graphical elements selected by the user are associated with branches attached to the root.

23. The method of claim 18, further comprising:

receiving a user activation of a publishing operation to be applied to one or more of the set of probe array results.

24. The method of claim 23, wherein:

the step of receiving a user activation includes the steps of receiving a user selection of one or more of the third set of graphical elements, and causing the probe array results corresponding to the user-selected ones of the third set of graphical elements to be published to the publish database.

25. A graphical user interface (GUI) for use with a computer display system having a processor coupled to a display device such that data is displayed on the display device in the GUI, comprising:

a first frame including a first set of graphical elements corresponding to at least one set of probe array results;

a second frame including a second set of graphical elements corresponding to a publish database and, in relation thereto, a third set of one or more graphical elements corresponding to those of the first set of graphical elements selected by a user, said publish database is in a format or organized in accordance with a schema to facilitate access by data analysis applications, data mining applications, data reporting applications, other data processing applications or any combination thereof; wherein the at least one set of probe array results is in a first format and the publisher is constructed and arranged to publish the first set of data in a second format.

26. The GUI of claim 25, wherein:

the first frame includes a data file view wherein the first and second sets set of graphical elements are arranged in a first tree structure.

27. The GUI of claim 26, wherein:

the first set of graphical elements is arranged in one branch of the first tree structure.

28. The GUI of claim 25, wherein:

at least one of the first set of graphical elements corresponds to a probe array result file.

29. The GUI of claim 25, wherein:

the second frame includes an active database view wherein the second set of graphical elements is associated with a root of a tree structure and the third set of one or more graphical elements corresponding to those of the first set of graphical elements selected by the user are associated with branches attached to the root.

30. A computer program product for providing a publish database comprising a computer usable medium storing control logic that, when executed on a computer system, performs a method comprising the steps of:

identifying at least one set of probe array results for publishing; and publishing the at least one set of probe array results as a first set of data in a publish database, said publish database is in a format or organized in accordance with a schema to facilitate access by data analysis applications, data mining applications, data reporting applications, other data processing applications or any combination thereof; wherein the at least one set of probe array results is in a first format and the publisher is constructed and arranged to publish the first set of data in a second format.

31. A computer system, comprising:

a processor; and a memory unit having stored therein a set of data management instructions that, when executed by the processor, performs a method for providing a publish database comprising the steps of identifying at least one set of probe array for publishing, and publishing the at least one set of probe array results as a first set of data in a publish database, said publish database is in a format or organized in accordance with a schema to facilitate access by data analysis applications, data mining applications, data reporting applications, other data processing applications or any combination thereof; wherein the at least one set of probe array results is in a first format and the publisher is constructed and arranged to publish the first set of data in a second format.

* * * * *